(12) United States Patent
Severin et al.

(10) Patent No.: US 10,221,198 B2
(45) Date of Patent: Mar. 5, 2019

(54) PREPARATION AND MEDICAL USE OF TRIAZENES

(71) Applicant: Ecole Polytechnique Federale De Lausanne (EPFL), Lausanne (CH)

(72) Inventors: Kay Severin, Lausanne (CH); Gregor Kiefer, Ecublens (CH)

(73) Assignee: Ecole Polytechnique Federale De Lausanne (EPFL), Lausanne (CH)

( * ) Notice: Subject to any disclaimer, the term of this patent is extended or adjusted under 35 U.S.C. 154(b) by 0 days.

(21) Appl. No.: 15/321,620

(22) PCT Filed: Jun. 27, 2014

(86) PCT No.: PCT/EP2014/001773
§ 371 (c)(1),
(2) Date: Dec. 22, 2016

(87) PCT Pub. No.: WO2015/197096
PCT Pub. Date: Dec. 30, 2015

(65) Prior Publication Data
US 2017/0158714 A1  Jun. 8, 2017

(51) Int. Cl.
*C07F 1/02* (2006.01)
*C07C 245/24* (2006.01)

(52) U.S. Cl.
CPC .............. *C07F 1/02* (2013.01); *C07C 245/24* (2013.01)

(58) Field of Classification Search
None
See application file for complete search history.

(56) References Cited

U.S. PATENT DOCUMENTS

| 2,373,800 A | 4/1945 | Acken et al. |
| 2010/0068178 A1 | 3/2010 | Gokaraju et al. |

FOREIGN PATENT DOCUMENTS

| EP | 2557075 A1 | 2/2013 |
| GB | 1569301 A | 6/1980 |

OTHER PUBLICATIONS

Bamberger et al. (1899) "Ueber die Einwirkung von Nitrosoarylen auf Asymmetrisch Alkylirte arylhydrazine," Berichte der deutschen chemischen Gesellschaft. 32(3):3554-3560.—Chemical formulas only.
Jones et al. (1969) "Solvolysis of sulfonic acid esters of triphenylvinyl alcohol by a heterolytic mechanism," J. Am. Chem. Soc. 91(15):4314-4315.
Kimball et al. (2002) "Triazenes: a versatile tool in organic synthesis," Angew. Chem. Int. Ed. 41:3338-3351.
Sieh et al. (1980) "Preparation of trialkyltriazenes. A comparison of the nitrogen-nitrogen bond rotation in trialkyltriazenes and aryldialkyltriazenes by variable temperature carbon—13 NMR," J. Am. Chem. Soc. 102:3883-3887.
Zollinger (1994) "Formation and Reactions of Triazenes," Ch. 13 In; Diazo Chemistry I. Wiley-VCH. Weinheim, Germany. pp. 385-404.
International Search Report with Written Opinion corresponding to International Patent Application No. PCT/EP2014/001773, dated Oct. 7, 2014.

*Primary Examiner* — Kamal A Saeed
(74) *Attorney, Agent, or Firm* — Leydig, Voit & Mayer, Ltd.

(57) ABSTRACT

The present invention relates to a novel method for preparing triazenes. Further, the invention relates to novel triazenes and the use of $N_2O$ for preparing a compound comprising a triazene group. Further, the invention relates to the use of the novel triazenes as a medicament, in particular in the treatment of cancer.

16 Claims, No Drawings

PREPARATION AND MEDICAL USE OF TRIAZENES

CROSS-REFERENCE TO RELATED APPLICATIONS

This application is a U.S. National Stage Application filed under 35 U.S.C. § 371 of International Application No. PCT/EP2014/001773, filed Jun. 27, 2014, which is hereby incorporated by reference in its entirety.

The present invention relates to a novel method for preparing triazenes. Further, the invention relates to novel triazenes and the use of $N_2O$ for preparing a compound comprising a triazene group. Further, the invention relates to the use of the novel triazenes as a medicament, in particular in the treatment of cancer.

Triazenes are valuable compounds in organic chemistry and numerous applications have been reported. For example, D. B. Kimball and M. M. Haley consider triazenes as "a versatile tool in organic synthesis" (Angew. Chem. Int. Ed. 41, 3338 (2002)). Triazenes have been used as multifunctional linkers in solid-phase synthesis, as removable directing groups for C—H activation, as protecting groups during the synthesis of complex natural products and of shape-persistent phenylacetylene-based systems, and for the controlled desaturation of unactivated aliphatic compounds.

In addition to their synthetic utility, triazenes have gained importance because of their biological activity. Inter alia, triazenes have been investigated extensively as potential antitumor drugs, and the triazenes dacarbazine and temozolomide are currently used in the clinic for the treatment of cancer.

Trisubstituted triazenes can be obtained by different synthetic routes.

H. Zollinger, Diazo Chemistry I; Wiley-VCH, Weinheim, pp. 385-404 (1994) relates to the formation and reactions of triazenes. A frequently used method for the synthesis of trisubstituted triazenes relies on the coupling of diazonium salts with secondary amines. In particular, an aromatic diazonium compound is allowed to react with a secondary amine containing alkyl, aryl or heteroaryl substituents.

A more specific method is described by D. H. Sieh, D. J. Wilbur, C. J. Michejda, J. Am. Chem. Soc. 102, 3883 (1980). An azide, such as benzyl azide or n-butyl azide, is allowed to react with a Grignard reagent or an organolithium compound, followed by alkylation with organohalides, such as methyl iodide, to obtain two constitutional isomers of the resulting triazenes.

Triazenes with alkyl or aryl substituents in position 1 are available by the known synthetic routes. The pharmacological research has focused on the more stable aromatic triazenes like described in EP 2 55 075 A1.

Certain triazenes, for example trisubstituted triazenes with alkenyl or alkynyl groups in position 1, are not easily accessible by the above methods due to the high instability of the required starting materials. 1-Azido-1-alkynes, for example, would decompose at low temperatures and the first spectroscopic characterization of such a compound was only achieved recently. Diazonium salts of alkenes and alkynes are likewise unstable.

Due to the numerous applications of substituted triazenes, in particular the possible use as a pharmaceutical active ingredient, there is still a need for new methods of preparing triazenes, in particular trisubstituted triazenes with alkenyl or alkynyl groups in position 1.

Hence, it was an object of the present invention to overcome the above-mentioned disadvantages.

It was an object of the present invention to provide a process for preparing triazenes with a high yield and/or a high grade of selectivity.

It was a further object of the invention to provide a method for preparing substituted triazenes wherein the method can be applied independently from the type of substituents. In particular, a method for preparing triazenes with specific substituents, preferably with non-aromatic substituents such as 1-alkenyl and 1-alkynyl groups, should be provided.

Thus, the above objectives are unexpectedly solved by the provision of a new synthetic approach for preparing substituted triazenes.

In said new approach, a compound according to Formula (II) is reacted with a compound of Formula (III) for preparing a substituted triazene.

Hence, a subject of the present invention is a method for preparing a triazene according to Formula (I)

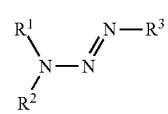

Formula (I)

by reacting a compound according to Formula (II)

  Formula (II)

$R^1R^2N(N_2O)M^1$ with a compound of Formula (III)

  Formula (III)

$R^3M^2$ wherein $R^1$ and $R^2$ independently are an organic residue $R^3$ is an organic residue, $M^1$ is a metal compound, preferably selected from Li, Na, K, and $M^2$ is a metal compound, preferably selected from Li, Na, K, MgCl, MgBr, MgI, ZnCl, ZnBr, ZnI, $ZnR^{3'}$, and $AlR^{3'}R^{3''}$, wherein $R^{3'}$ and $R^{3''}$ are independently an organic residue.

It was found that the present process allows advantageous yield and selectivity of the resulting triazenes. Further, simple reaction conditions can be applied and the usage of potentially hazardous and explosive diazonium salts can be advantageously avoided. Additionally, besides alkyl and aryl substituted triazines, also 1-alkenyl and 1-alkynyl triazines are easily accessible.

Another subject of the invention is the use of $N_2O$ for preparing a compound comprising a triazene group.

The invention further relates to a compound according to Formula (I) wherein $R^3$ is —C≡C—$R^5$, wherein $R^5$ is an organic residue; or $R^3$ is —$R^6$C═$CR^7R^8$, wherein $R^6$, $R^7$, $R^8$ are independently an organic residue, and with the proviso that the C═C-bond is not part of an aromatic system. Another subject is a compound according to Formula (I) for use as a medicament, in particular for use in the treatment of cancer.

During the processes described in the present invention, a compound according to Formula (II) can be an important intermediate. Hence, the present invention is directed to a compound according to Formula (II) and a method for preparing said compound.

DETAILED DESCRIPTION OF THE INVENTION

The present method for preparing a triazene according to Formula (I)

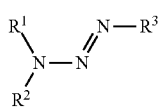

Formula (I)

comprises reacting a compound according to Formula (II) with a compound of Formula (III)
wherein
$R^1$ and $R^2$ independently are an organic residue
$R^3$ is an organic residue,
$M^1$ is a metal compound, preferably selected from Li, Na, K, and
$M^2$ is a metal compound, preferably selected from Li, Na, K, MgCl, MgBr, MgI, ZnCl, ZnBr, ZnI, $ZnR^{3'}$, and Al $R^{3'}R^{3''}$, wherein $R^{3'}$ and $R^{3''}$ are independently an organic residue.

"Organic residue" generally refers any residue known in organic chemistry. Preferably, the skeleton of the organic residue contains predominately carbon atoms, nitrogen atoms and/or oxygen.

In a preferred embodiment, $R^1$ and $R^2$ can be independently a substituted or unsubstituted aryl group, or a substituted or unsubstituted hetero aryl group, or a substituted or unsubstituted alkyl group with 1 to 16 carbon atoms, a substituted or unsubstituted cyclic alkyl group with 3 to 12 carbon atoms, a substituted or unsubstituted cyclic alkenyl group with 3 to 12 carbon atoms, a substituted or unsubstituted alkenyl group with 2 to 16 carbon atoms, or a substituted or unsubstituted alkynyl group with 2 to 16 carbon atoms, wherein in the substituted or unsubstituted alkyl group with 1 to 16 carbon atoms, the substituted or unsubstituted cyclic alkyl group with 3 to 12 carbon atoms, the substituted or unsubstituted cyclic alkyl group with 3 to 12 carbon atoms, the substituted or unsubstituted alkenyl group with 2 to 12 carbon atoms, or the substituted or unsubstituted alkynyl group with 2 to 16 carbon atoms one or more —$CH_2$— group(s) can be substituted by a —O—, —S—, —$NR^4$—, or $SiR^4R^{4'}$ to form an ether, a thioether, a secondary or tertiary amine, or a silylether and wherein $R^4$ and $R^{4'}$ are independently hydrogen, an alkyl group with 1 to 6 carbon atoms or a cyclic alkyl group with 3 to 6 carbon atoms or wherein $R^1$ and $R^2$ together with the nitrogen to which $R^1$ and $R^2$ are attached form a hetero cycle with 3 to 7 carbon atoms.

An unsubstituted aryl group refers to a residue with an aromatic skeletal structure, wherein the ring atoms of the aromatic skeletal structure are carbon atoms.

Examples for aryl groups are phenyl, biphenyl, triphenyl, tetraphenyl, pentaphenyl, hexaphenyl, heptaphenyl, naphthyl, binaphthyl, ternapthyl, tetrahydronaphthyl, anthranyl, phenantranyl, pentacenyl, azulenyl, fluorenyl, indanyl, phenalenyl, acenaphthyl, acephenantrylenyl aceantrylenyl, pentalenyl, indyl, pyryl, chrysenyl, naphthacenyl, perylenyl, picenyl, rubincenyl, coronenyl, pyranthrenyl, ovalenyl, hexacenyl, and heptacenyl. Preferred are phenyl, biphenyl and naphthyl, more preferably phenyl and naphthyl, in particular phenyl.

An unsubstituted heteroaryl group refers to a residue with an aromatic skeletal structure, wherein one or more of the ring atoms of the aromatic skeletal structure are not carbon atoms but hetero atoms such as nitrogen, oxygen, sulphur and/or phosphor.

Examples for heteroaryl groups are pyrryl, pyrrazolyl, imidazolyl, triazolyl, furyl, isooxalyl, oxalyl, oxadiazolyl, thienyl, isothiazolyl, thiazolyl, thiadiazalyl, tetrazolyl, pyridyl, pyrazidyl, pyrazyl, pyrimidyl, triazolyl, indolyl, isoindolyl, benzofuranyl, benzothienyl, benzimidazyl, indazolyl, quinolinyl, isoquinolin, cinnolinyl, quinaxolinyl quinoxalinyl, triazinyl, tetrazinyl, acridinyl, purinyl, and pteridinyl.

In another preferred embodiment, the aryl group or hetero aryl group can bear one or more substituents. Examples for substituents are unsubstituted or substituted alkyl groups with 1 to 6 carbon atoms, unsubstituted or substituted alkoxy groups with 1 to 6 carbon atoms, aryloxy groups, optionally protected amines, optionally protected monoalkyl amines, optionally protected monoarylamines, dialkylamines, diarylamines, silyl ethers, halogens or optionally protected hydroxyl groups.

Protection groups for amines or monosubstituted amines are for example Boc (tert-butyloxycarbonyl), Z or Cbz (benzyloxycarbonyl), benzyl, benzhydryl, and Fmoc (fluorenylmethylenoxycarbonyl).

Protection groups for hydroxyl groups are for example esters, such as benzoic acid esters or pivalic acid esters, and trisubstituted silylethers, such as trimethylsilylether, triethylsilylether, tert-butyldimethylsilylether and tert-butyl diphenylsilylether.

In a preferred embodiment, $R^1$ and $R^2$ are independently a substituted or unsubstituted alkyl group with 1 to 16 carbon atoms, a substituted or unsubstituted cyclic alkyl group with 3 to 12 carbon atoms wherein one or more of the —$CH_2$— group(s) can be substituted by —O—, —S— or —$NR^4$—, to form an ether, a thioether or a tertiary amine, and wherein $R^4$ is an alkyl group with 1 to 6 carbon atoms or a cyclic alkyl group with 3 to 6 carbon atoms.

A substituted alkyl or cyclic alkyl group is an alkyl or cyclic alkyl group substituted by a further group. Examples of substituents are further alkyl, alkenyl, alkynyl, halogen, alkoxy, aryloxy groups, optionally protected amines, optionally protected monoalkyl amines, optionally protected monoarylamines, dialkylamines, diarylamines, silyl ethers, halogens or optionally protected hydroxyl groups, esters and amides of carboxylic acids, unsubstituted and substituted aryl groups, and unsubstituted and substituted hetero aryl groups.

It is preferred that $R^1$ and $R^2$ are equal. Alternatively preferred $R^1$ does not correspond to $R^2$.

In a preferred embodiment, $R^1$ and $R^2$ are independently an alkyl group with 1 to 6 carbon atoms, more preferably with 1 to 4 carbon atoms or a cyclic alkyl group with 3 to 8 carbon atoms, preferably 3 to 6 carbon atoms.

Alkyl groups with 1 to 6 carbon atoms can for example include methyl, ethyl, propyl, isopropyl, butyl, isobutyl, and tert.-butyl, pentyl, 2-pentyl, 3-pentyl, hexyl, 2-hexyl and 3-hexyl.

Preferred are isopropyl, isobutyl, tert-butyl, pentyl, 2-pentyl, 3-pentyl, hexyl, 2-hexyl and 3-hexyl, in particular isopropyl. In a preferred embodiment methyl is particularly preferred. In a preferred embodiment ethyl is particularly preferred.

Cyclic alkyl groups with 3 to 8 carbon atoms include cyclopropyl, cyclobutyl, cyclopentyl, cyclohexyl, cycloheptyl and cyclooctyl, preferably cyclopropyl, cyclopentyl, cyclohexyl and cycloheptyl, more preferably cyclopentyl and cyclohexyl.

It is preferred that $R^1$ and $R^2$ both are not ethyl. Further, $R^1$ and/or $R^2$ do preferably not contain an acyl group.

In an alternative embodiment, $R^1$ and $R^2$ together with the nitrogen to which $R^1$ and $R^2$ are attached can form a hetero cycle with 3 to 7 carbon atoms. It is preferred that a hetero cycle with nitrogen (being part of the triazene) and 4 or 5 carbon atoms is formed.

$R^3$ can preferably be a substituted or unsubstituted aryl group, or a substituted or unsubstituted hetero aryl group, or a substituted or unsubstituted alkyl group with 1 to 16 carbon atoms, a substituted or unsubstituted cyclic alkyl group with 3 to 12 carbon atoms, a substituted or unsubstituted alkenyl group with 2 to 16 carbon atoms, or a substituted or unsubstituted alkynyl group with 2 to 16 carbon atoms, wherein in the substituted or unsubstituted alkyl group with 1 to 16 carbon atoms, the substituted or unsubstituted cyclic alkyl group with 3 to 12 carbon atoms, the substituted or unsubstituted cyclic alkyl group with 3 to 12 carbon atoms, the substituted or unsubstituted alkenyl group with 2 to 12 carbon atoms, or the substituted or unsubstituted alkynyl group with 2 to 16 carbon atoms, one or more —$CH_2$— group(s) can be substituted by a —O—, —S—, —$NR^4$— or $SiR^4R^{4'}$, to form an ether, a thioether, a secondary or tertiary amine, or a silylether and wherein $R^4$ and $R^{4'}$ are independently hydrogen, an alkyl group with 1 to 6 carbon atoms or a cyclic alkyl group with 3 to 6 carbon atoms.

For $R^{3'}$ and $R^{3''}$, the same explanations as above for $R^3$ apply. It is not obligatory that $R^3$, $R^{3'}$ and $R^{3''}$ are the same specific group. For example, $R^3$ can be phenyl, while $R^{3'}$ is ethyl and $R^{3''}$ is propyl. For example, a compound according to Formula (III) can be $(Ph)_2Zn$ or PhZnEt. It is preferred that $R^3$, $R^{3'}$ and $R^{3''}$ are the same group.

In a preferred embodiment of the invention the triazene according to Formula (I) is a trisubstituted triazene; i.e. $R^1$, $R^2$ and $R^3$ are not hydrogen.

Generally, $M^1$ is a metal compound. A metal compound can be a compound which contains at least one element being a member of the alkaline metal group, the alkaline earth metal group, the transition metal group, the lanthanide group, the actinide group, the metalloid group such as boron and silicon, or the post transition metal group comprising aluminium. The metal compound can be present as an organometallic compound.

Generally, the metal compound can be present in any suitable form, e.g. in any suitable oxidation state. It is preferred that the metal compound is present in form of an element or in the form of a positive ion. This ion may form the counter ion to the negatively charged residue according to Formula (II).

In a preferred embodiment, $M^1$ is a member of the alkaline metal group or the alkaline earth metal group, preferably the alkaline metal group. More preferably, $M^1$ is selected from Li, Na and K, more preferably Li and Na, in particular Li.

Generally, $M^2$ and is also a metal compound as described above for $M^1$. It is preferred that the metal compound $M^2$ is present as a (partially) positively charged compound bonded or associated to the negatively charged organic residue $R^3$ according to Formula (III).

In a preferred embodiment the compound according to Formula (III) forms an organometallic compound, such as an organomagnesium compound (Grignard compound) or an organozinc compound, preferably an organomagnesium compound. It is preferred that $M^2$ is MgCl, MgBr, or MgI, especially MgCl and MgBr.

Alternatively, $M^2$ is a member of the alkaline metal group, the alkaline earth metal group, preferably the alkaline metal group. More preferably $M^2$ is selected from Li, Na and K, more preferably Li and Na, in particular Li.

According to the present method, a compound according to Formula (II) is reacted with a compound according to Formula (III) to give a triazene according to Formula (I).

The compound according to Formula (III) can be obtained, for example, by mixing magnesium with a non-protic organic solvent free from water and a compound composed of organic residue $R^3$ bonded to a halogen such as chloride, bromide or iodide. Suitable solvents are, for example, ethers such as diethyl ether or tetrahydrofuran. Further, the reaction can preferably be carried out under an inert gas atmosphere.

Alternatively, in case of $R^3$ being a terminal alkynyl residue, a compound according to Formula (III) can be obtained by reacting the respective alkyne with a Grignard reagent, for example an alkylmagnesium halogenide such as ethylmagnesium chloride, under the release of the corresponding alkyl such as ethane. For this purpose, a solution of the respective alkyne can be provided in a non-protic organic solvent free from water and the alkylmagnesium halogenide, preferably as a solution or suspension in the same solvent, can be added. Suitable solvents are, for example, ethers such as diethyl ether or tetrahydrofuran, in particular tetrahydrofuran. Further, the reaction can preferably be carried under an inert gas atmosphere. Preferably, the reaction can be carried out at room temperature, i.e. 23° C. After the completion of the addition of the alkylmagnesium halogenide, the reaction can preferably be warmed to 50° C. for about 1 hour to complete the reaction.

In a preferred embodiment of the present method, a solution or suspension of a compound according to Formula (II) in a first non-protic solvent—preferably essentially free of water—is provided, preferably under an atmosphere of an inert gas. Suitable first non-protic solvents can be alkanes such as pentane, hexane or heptane, cyclic alkanes such as cyclic pentanes or cyclic hexanes, and ethers such diethyl ether, tert-butyl methyl ether or tetrahydrofuran. To said solution/suspension a compound according to Formula (III), which can be dissolved, preferably completely dissolved, in a second non-protic solvent free from water, is added. The second solvent can be the same as the first solvent or different to the first solvent. Preferably, ethers such diethyl ether, tert-butyl methyl ether or tetrahydrofuran are used as second solvent.

The step of reacting the compound according to Formula (II) with a compound according to Formula (III) to give a compound according to Formula (I) can be preferably carried out at increased temperatures, preferably between 25° C. to 65° C., more preferably between 30° C. and 55° C. It is further preferred that the temperature is elevated after the addition, preferably the complete addition, of the solution of a compound according to Formula (III) to the solution/dispersion of compound according to Formula (II). Generally, the reaction time can be between 10 and 360 min, preferably between 60 and 240 minutes. The reaction can be carried out between 30° C. and 70° C., preferably between 40° C. and 60° C.

In a preferred embodiment, the ratio of the compound according to Formula (II) to the compound according to Formula (III) is from 1:1 to 1:3, preferably from 1:1.2 to 1:2.5, more preferably from 1:1.4 to 1:2.2, in particular from 1:1.5 to 1:2.

Preferably, the compound according to Formula (II)

$$R^1R^2N(N_2O)M^1 \quad \text{Formula (II)}$$

is prepared by reacting a compound according to Formula (IV)

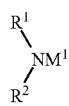

Formula (IV)

with nitrous oxide.

The above reaction involves nitrous oxide which is also known as 'laughing gas'.

This name results from the euphoric effect in case of inhaling the gas. Nitrous oxide is represented by the formula $N_2O$. It is reported to have a dipole moment of 0.16083 D ($5.365 \cdot 10^{-31}$ C·m). Inter alia, nitrous oxide is used for its anesthetic and analgesic effects in surgery and dentistry. However, nitrous oxide is rarely used in synthetic organic chemistry. Chemical reactions with $N_2O$ typically proceed by oxygen atom transfer and liberation of nitrogen ($N_2$). In contrast, there are very few examples about the utilization of nitrous oxide as nitrogen donor, in particular in the context of synthetic organic chemistry.

A compound according to Formula (IV) can, for example, be obtained by reacting the corresponding amine ($R^1R^2NH$) with the respective alkaline metal. Alternatively the corresponding amine ($R^1R^2NH$) can be reacted with an organometallic compound such as buthyllithium (BuLi) or phenyllithium (PhLi).

It is preferred that a compound according to Formula (IV) is dissolved, preferably completely dissolved, in a non-protic solvent, which is preferably essentially free from water. Suitable solvents are, for example, ethers such as diethyl ether or tetrahydrofuran. Further, the solution of a compound according to Formula (IV) is preferably stirred under a nitrous oxide atmosphere. Alternatively preferred, nitrous oxide can be fed into a solution of a compound according to Formula (IV).

The reaction of nitrous oxide with a compound according to Formula (IV) is preferably carried out at temperatures of −10° C. to 50° C., preferably of 5° C. to 40° C., more preferably of 15° C. to 35° C., in particular of 20 to 27° C. Further, completion of the reaction takes preferably from 0.5 to 12 hours, more preferably from 1 to 9 hours, especially from 2 to 6 hours.

The compound according to Formula (II) can optionally precipitate from the non-protic solvent, preferably in form of a colourless or white solid. Further, said compound can optionally be isolated, for example by filtration, washed with non-protic solvent, for example tetrahydrofuran dried under reduced pressure.

Alternatively, after completion of the reaction of nitrous oxide with a compound according to Formula (IV) in a non-protic solvent, the resulting compound according to Formula (II) in the non-protic solvent can preferably be further reacted without isolation of the compound according to Formula (II). For this purpose, nitrous oxide can optionally be replaced by an inert gas after the completion of the reaction. Examples for such inert gases are nitrogen or argon.

In one embodiment, a triazene according to Formula (I) can be obtained by reacting a compound according to Formula (IV) with nitrous oxide and a compound according to Formula (III). This reaction can be conducted as a so called "one-pot-reaction". For this purpose, a compound according to Formula (III) and a compound according to Formula (IV) can be dissolved, preferably completely dissolved, e.g. in a non-protic organic solvent, preferably essentially free from water, or a mixture of such solvents and allowed to react with nitrous oxide. Suitable non-protic solvents correspond to the non-protic solvents free from water described above. Tetrahydrofuran can be used in particular.

Optionally a compound according to Formula (II) is obtained in the above-mentioned manner and subsequently the residual nitrous oxide is removed/substituted. Subsequently, the compound according to Formula (II) is reacted with a compound according to Formula (III) in a manner as described above to obtain a triazene according to Formula (I).

A further subject of the invention is the use of $N_2O$ for preparing a compound comprising a triazene group. In a preferred embodiment, $N_2O$ is used for preparing a compound according to Formula(e) (I) and/or (II).

Generally, the use of $N_2O$ can be carried out as described in the above methods. Further, all explanations given above or below with regard to the compounds of the present invention or with regard to the process of the present invention also relate to the use of the present invention. For example, as illustrated above the process of the present invention is particularly preferred for producing trisubstituted triazenes. Hence, $N_2O$ is preferably used for preparing trisubstituted triazenes according to Formula (I).

It was found that nitrous oxide mediates the coupling of compounds according to Formula (IV) and compounds according to Formula (III) while serving as nitrogen donor. Despite the very inert character of nitrous oxide, the reactions can be performed in solution under mild condition.

Examples of triazines containing aromatic residues prepared by the present process are

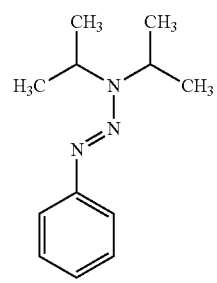

P1

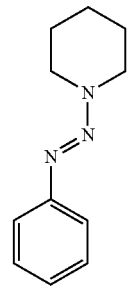

P2

-continued

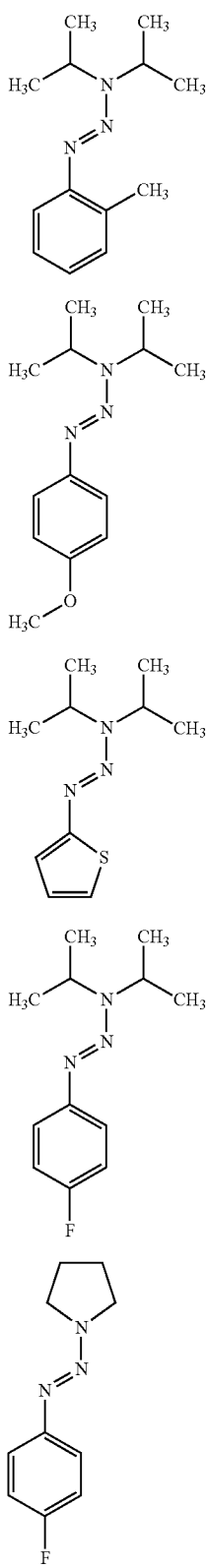

P3
P4
P5
P6
P7

An advantage of the present process is that the potentially hazardous aryl diazonium salts can be avoided.

Another subject of the present invention is a compound according to Formula (I),

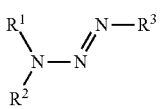

Formula (I)

wherein $R^1$ and $R^2$ independently are an organic residue, and $R^3$ is —C≡C—$R^5$, wherein $R^5$ is an organic residue; or $R^3$ is —$R^6$C═C$R^7R^8$, wherein $R^6$, $R^7$, $R^8$ are independently an organic residue and with the proviso that the C═C-bond is not part of an aromatic system.

In a preferred embodiment of the compounds of the present invention, $R^1$ and $R^2$ are defined as described above.

Preferably $R^1$ and $R^2$ are ethyl or methyl, in particular methyl.

Further, in a preferred embodiment of the compounds of the present invention $R^3$ is —C≡C—$R^5$ with $R^5$ being an organic residue; or $R^3$ is —$R^6$C═C$R^7R^8$ with $R^6$, $R^7$, $R^8$ being independently an organic residue and with the proviso that the C═C-bond is not part of an aromatic system.

In a preferred embodiment of the compounds of the present invention, $R^5$ is hydrogen, a trisubstituted silyl group, a substituted or unsubstituted aryl group, or a substituted or unsubstituted hetero aryl group, or a substituted or unsubstituted alkyl group with 1 to 16 carbon atoms, or a substituted or unsubstituted cyclic alkyl group with 3 to 12 carbon atoms, wherein in the substituted or unsubstituted alkyl group with 1 to 16 carbon atoms, the substituted or unsubstituted cyclic alkyl group with 3 to 12 carbon atoms, optionally one or more —CH$_2$— group(s) can be substituted by —O—, —S—, —NR$^4$—, or SiR$^4$R$^{4'}$ to form an ether, a thioether, a secondary or tertiary amine, or a silylether and wherein $R^4$ and $R^{4'}$ are independently hydrogen, an alkyl group with 1 to 6 carbon atoms or a cyclic alkyl group with 3 to 6 carbon atoms.

A trisubstituted silyl group is a silyl group wherein all three substituents are independently a substituted or unsubstituted aryl group, a substituted or unsubstituted hetero aryl group, a substituted or unsubstituted alkyl group with 1 to 16 carbon atoms, a substituted or unsubstituted cyclic alkyl group with 3 to 12 carbon atoms as described above.

A substituted or unsubstituted aryl group, a substituted or unsubstituted hetero aryl group, a substituted or unsubstituted alkyl group with 1 to 16 carbon atoms, a substituted or unsubstituted cyclic alkyl group with 3 to 12 carbon atoms are defined as described above.

In a preferred embodiment of the compounds of the present invention, $R^5$ is a phenyl or a phenyl with one or more substituents. Examples of substituents are alkyl groups, preferably with 1 or 2 carbon atoms, substituted alkyl groups such as trifluormethyl, alkoxy groups such as methoxy or ethoxy, aryloxy groups such as phenoxy, amines, monoalkyl substituted amines, monoaryl substituted amines, dialkyl substituted amines, diaryl substituted amines, monoalkyl monoaryl substituted amines, trisubstituted silylgroups, such as trimethylsilyl, or halgogenides such as fluorine.

In a preferred embodiment of the compounds of the present invention, $R^5$ is an alkyl group with 1 to 6 carbon atoms, wherein optionally one or more —CH$_2$— group(s) can be substituted by —O— or —NR$^4$—, to form an ether, or a secondary or tertiary amine, and wherein $R^4$ is hydrogen, an alkyl group with 1 or 2 carbon atoms or a cyclic alkyl group with 3 carbon atoms, preferably methyl. In case of a substitution of a $CH_2$-group by —O—, —S— —$NR^4$—, or $SiR^4R^{4'}$ it is preferred that the substitution is at the β-position to the carbon-carbon triple bond.
Examples for compounds with $R^3$ being —C≡C—$R^5$ are
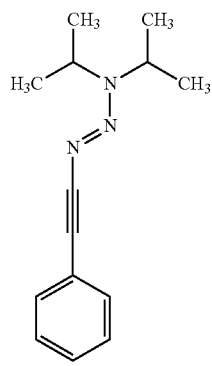
1
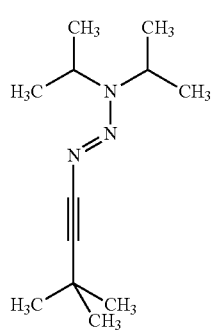
2
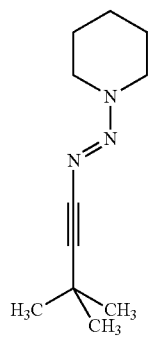
3
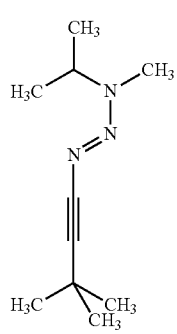
4
-continued
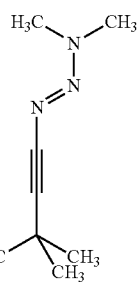
5
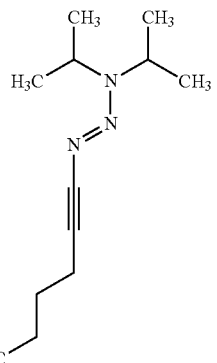
6
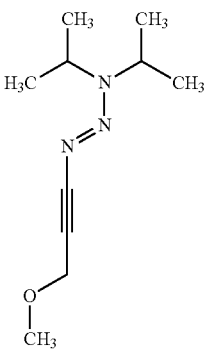
7
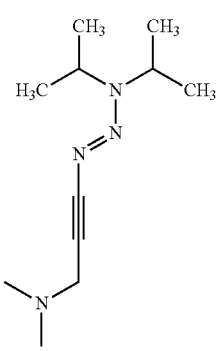
8

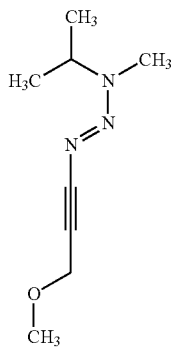

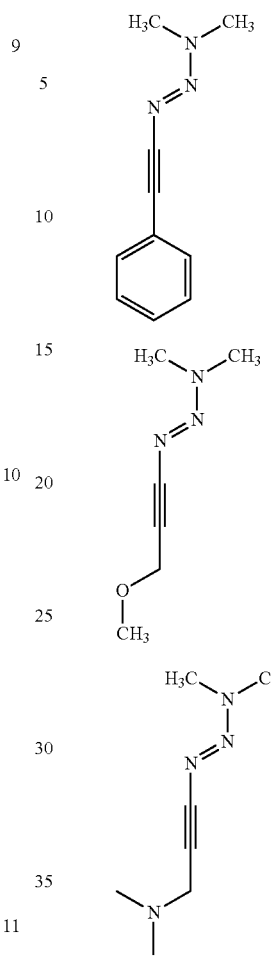

In a further preferred embodiment of the compounds of the present invention, in Formula (I) $R^6$, $R^7$ and $R^8$ are independently hydrogen, a trisubstituted silyl group, a substituted or unsubstituted aryl group, or a substituted or unsubstituted hetero aryl group, or a substituted or unsubstituted alkyl group with 1 to 16 carbon atoms, or a substituted or unsubstituted cyclic alkyl group with 3 to 12 carbon atoms, wherein in the substituted or unsubstituted alkyl group with 1 to 16 carbon atoms, the substituted or unsubstituted cyclic alkyl group with 3 to 12 carbon atoms, one or more —CH$_2$— group(s) can be substituted by —O—, —S—, —NR$^4$—, or SiR$^4$R$^{4'}$ to form an ether, a thioether, a secondary or a tertiary amine, or a silylether and wherein $R^4$ and $R^{4'}$ are independently hydrogen, an alkyl group with 1 to 6 carbon atoms or a cyclic alkyl group with 3 to 6 carbon atoms, or wherein $R^6$ and $R^7$ or $R^6$ and $R^8$ together with the —C═C— double bond to which $R^6$ and $R^7$ or $R^6$ and $R^8$ are attached form a cyclic substituted or unsubstituted alkenyl group or a substituted or unsubstituted cyclic hetero alkenyl group and the remaining $R^7$ or $R^8$ is defined as above.

Further, in case $R^3$ is —R$^6$C═CR$^7$R$^8$ the present compound refers to all possible (Z)- and (E)-isomers thereof.

It is preferred that at least one of $R^6$, $R^7$ and $R^8$ is hydrogen.

A trisubstituted silyl group is preferably defined as described above.

A substituted or unsubstituted aryl group, a substituted or unsubstituted hetero aryl group, a substituted or unsubstituted alkyl group with 1 to 16 carbon atoms, a substituted or unsubstituted cyclic alkyl group with 3 to 12 carbon atoms are defined as described above.

In a preferred embodiment, one or more of $R^6$, $R^7$ and $R^8$ is a phenyl or a phenyl with one or more substituents. Examples of substituents are alkyl groups, preferably with 1 or 2 carbon atoms, substituted alkyl groups such as trifluormethyl, alkoxy groups such as methoxy or ethoxy, or fluorine.

In a preferred embodiment, one or more of $R^6$, $R^7$ and $R^8$ is an alkyl group with 1 to 6 carbon atoms wherein optionally one or more —$CH_2$— group(s) can be substituted by —O—, —S—, —$NR^4$— or $SiR^4R^{4'}$ to form an ether, a thioether, a tertiary amine, or a silylether and wherein $R^4$ and $R^{4'}$ are independently an alkyl group with 1 or 2 carbon atoms or a cyclic alkyl group with 3 carbon atoms. In case of a substitution of a —$CH_2$-group by —O—, —S—, —$NR^4$—, or $SiR^4R^4$ it is preferred that the substitution is at the β-position to the carbon-carbon double bond.

In an alternative preferred embodiment of the invention, $R^6$ and $R^7$ or $R^6$ and $R^8$ together with the —C═C— double bond to which $R^6$ and $R^7$ or $R^6$ and $R^8$ are attached form a substituted or unsubstituted cyclic alkenyl group or a cyclic substituted or unsubstituted hetero alkenyl group. Further, the substituted or unsubstituted cyclic alkenyl group or a substituted or unsubstituted cyclic hetero alkenyl group can comprise one or more further double bond(s) as long as no aromatic system is formed.

In a preferred embodiment, $R^6$ and $R^7$ or $R^6$ and $R^8$ can be selected such that an unsubstituted cyclic alkenyl group or an unsubstituted cyclic hetero alkenyl group is formed.

Alternatively, it is preferred that $R^6$ and $R^7$ or $R^6$ and $R^8$ can be selected such that a substituted cyclic alkenyl group or a substituted cyclic hetero alkenyl group is formed. Examples for substituents are alkyl with 1 to 4 carbon atoms, and alkoxy with 1 or 2 carbon atoms.

Examples for compounds with $R^3$ being —$R^6C$═$CR^7R^8$ are

16

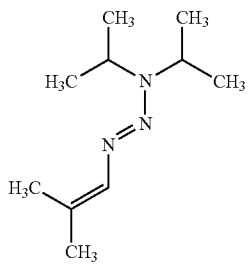

17

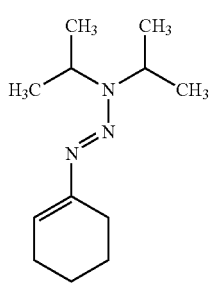

18

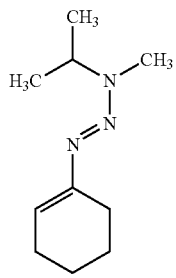

19

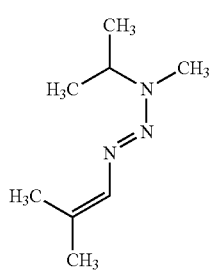

20

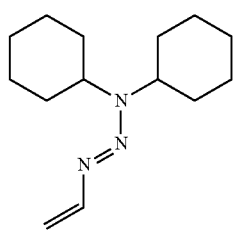

21

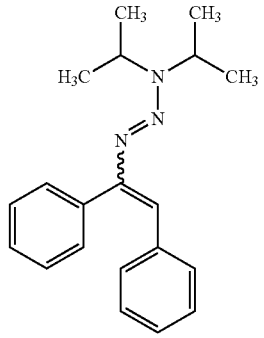

22

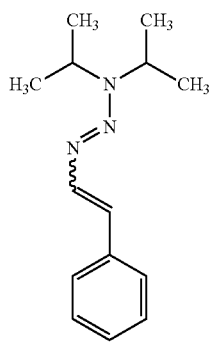

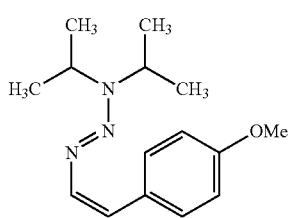
23

Further, the present invention relates to the compounds according to Formula (I) for use as a medicament.

A further subject of the invention is the compound according to Formula (I) for use in the treatment of cancer, i.e. for use in an anti-tumor therapy.

An anti-tumor therapy might be understood as a therapy based on active pharmaceutical ingredients for the treatment of carcinosis. The compounds of the present invention are preferably cytostatic. Generally, a cytostatic drug is a compound which selectively prevents or reduces the cell growth or inhibits the cell division of the malignant cell. Preferably, the cytostatic drug affects healthy cells as little as possible. Generally, the cell division of malignant cells is reported to be faster than that of healthy cells. Due to this ability the malignant cells are more sensitive to any interference of the cell growth and division. The present triazenes show a significant cytotoxicity, for example to the cancer cell lines A2780 (ovarian cancer) and MDA-MB-231 (invasive breast cancer).

A further subject of the present invention is a compound according to Formula (II), $R^1R^2N(N_2O)M^1$  Formula (II)

wherein
$R^1$ and $R^2$ independently are an organic residue, and
$M^1$ is a metal compound, preferably selected from Li, Na and K.

In a preferred embodiment, $R^1$, $R^2$ and $M^1$ correspond to the residues as described above.

Examples of $N_2O$-adducts are

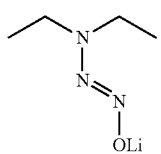
I1

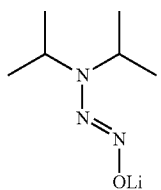
I2

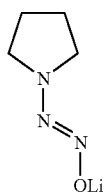
I3

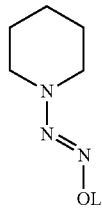
I4

Further, the present invention relates to a method for preparing a compound according to Formula (II)

$R^1R^2N(N_2O)M^1$ 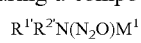 Formula (II)

by reacting $R^1R^2N$-$M^1$ with nitrous oxide, wherein
$R^1$ and $R^2$ independently are an organic residue, and
$M^1$ is a metal compound, preferably selected from Li, Na, and K.

Reacting $R^1R^2N$-$M^1$ with nitrous oxide can be preferably carried out in a solvent, preferably in a non-protic solvent free from water or a mixture of non-protic solvent free from water. For this purpose, a $R^1R^2N$-$M^1$ can be dissolved, preferably completely dissolved, in the solvent or the mixture of solvents such as ethers such as diethyl ether or tetrahydrofuran, or alkanes such as cyclopentane, pentane or hexane. Further, the solution of a compound according to Formula (IV) is preferably stirred under a nitrous oxide atmosphere. Alternatively preferred, nitrous oxide can be fed into the solution of R'R²N-M¹. The reaction of nitrous oxide with a $R^1R^2N$-$M^1$ is preferably carried out at temperatures of −10° C. to 50° C., preferably of 5° C. to 40° C., more preferably of 15° C. to 35° C., in particular of 20° C. to 27° C. Further, the completion of the reaction can preferably take 0.5 to 12 hours, more preferably 1 to 9 hours, especially 2 to 6 hours.

An example of a particularly preferred reaction scheme is as follows.

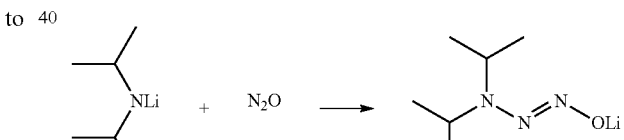

The invention can be illustrated by the following examples.

EXAMPLES

General Procedure for the Synthesis of Triazenes

The corresponding lithium amide (1.0 eq.) was dissolved in THF to form a 0.4 M solution. The resulting solution was stirred vigorously under an atmosphere of $N_2O$ for 4 h at 23° C. A white precipitate formed. The $N_2O$ atmosphere was then replaced by an atmosphere of dry $N_2$. Further, under continuous stirring the corresponding Grignard reagent in THF (2.0 eq.) was added which resulted in the formation of a yellow solution. After the completion of the addition of the Grignard reagent, the solution was stirred for 4 h at 50° C.

Unless stated differently, the product was isolated as follows. The mixture was quenched with water (15-20 mL), extracted with ethyl acetate (3×15-20 mL) and the unified organic phases were dried over anhydrous magnesium sulfate. A centrifuge was used to accelerate phase separation.

After filtration and removal of the solvent under reduced pressure, the product was obtained in sufficient purity or purified as stated below.

Compound P1: 3,3-Diisopropyl-1-phenyltriaz-1-ene

The product was synthesized from lithium diisopropylamide (2.0 mmol, 214 mg), $N_2O$ and phenylmagnesium chloride in THF (1.89 M, 4.0 mmol, 2.12 mL, 2.0 eq.) according to the general procedure. The crude product was distilled under vacuum at 80° C. using a cold finger. The product was obtained as a pale yellow, crystalline solid (385 mg, yield: 94%).

$^1$H NMR (400 MHz, $CDCl_3$, 0° C.) δ: 7.50-7.47 (m, 2H, 2×$CH_{ar}$), 7.40-7.35 (m, 2H, 2×$CH_{ar}$), 7.18-7.13 (m, 1H, $CH_{ar}$), 5.51-5.25 (m (br), 1H, CH), 4.14-3.87 (m (br), 1H, CH), 1.57-1.30 (m (br), 6H, 2×$CH_3$), 1.39-1.06 (m (br), 6H, 2×$CH_3$);

$^{13}$C NMR (100 MHz, $CDCl_3$, 0° C.) δ: 151.7 ($C_{ar}$), 128.9 (2×$CH_{ar}$), 124.8 ($CH_{ar}$), 120.3 (2×$CH_{ar}$), 48.5 (br, CH), 45.5 (br, CH), 24.3 (br, 2×$CH_3$), 19.7 (br, 2×$CH_3$);

HRMS (ESI-TOF): Simulated (MH+) 206.1652. found 206.1655.

Compound P2: 1-(Phenyldiazenyl)piperidine

The product was synthesized from lithium piperidinide (2.0 mmol, 182 mg), $N_2O$ and phenylmagnesium chloride in THF (1.89 M, 4.0 mmol, 2.12 mL, 2.0 eq.) according to the general procedure. The crude product was distilled under vacuum at 80° C. using a cold finger. The product was obtained as a pale yellow, crystalline solid (268 mg, yield: 71%).

$^1$H NMR (400 MHz, $CDCl_3$, 0° C.) δ: 7.53-7.50 (m, 2H, 2×$CH_{ar}$), 7.43-7.38 (m, 2H, 2×$CH_{ar}$), 7.24-7.20 (m, 1H, $CH_{ar}$), 3.83-3.80 (m (br), 4H, 2×$NCH_2$), 1.75-1.70 (m (br), 6H, 3×CH2;

$^{13}$C NMR (100 MHz, $CDCl_3$, 0° C.) δ: 150.7 ($C_{ar}$), 128.9 (2×$CH_{ar}$), 125.6 ($CH_{ar}$), 120.4 (2×$CH_{ar}$), 50.2 (br, $NCH_2$), 46.1 (br, $NCH_2$), 25.2 (br, 2×$CH_2$), 24.3 ($CH_2$);

HRMS (ESI-TOF): Simulated (MH+) 190.1339. found 190.1341.

Compound P3: 3,3-Diisopropyl-1-o-tolyltriaz-1-ene

The product was synthesized from lithium diisopropylamide (2.0 mmol, 214 mg), $N_2O$ and o-tolylmagnesium chloride in THF (0.94 M, 4.26 mL, 2.0 eq.) according to the general procedure. The crude product was distilled under vacuum at 80° C. using a cold finger. The product was obtained as a pale yellow, crystalline solid (404 mg, yield: 92%).

$^1$H NMR (400 MHz, $CDCl_3$, 0° C.) δ: 7.38-7.35 (m, 1H, $CH_{ar}$), 7.17-7.15 (m, 1H, $CH_{ar}$), 7.15-7.12 (m, 1H, $CH_{ar}$), 7.03-6.99 (m, 1H, $CH_{ar}$), 5.29-5.05 (m (br), 1H, CH), 4.15-3.85 (m (br), 1H, CH), 2.42 (s, 3H, $CH_3$ (tol.)), 1.56-1.02 (m (br), 12H, 4×$CH_3$).

$^{13}$C NMR (100 MHz, CDCl3, 0° C.) δ: 149.5 ($C_{ar}$), 132.4 ($C_{ar}$), 130.6 ($CH_{ar}$), 126.2 ($CH_{ar}$), 124.7 ($CH_{ar}$), 116.3 (CHO, 49.1 (br, CH), 46.2 (br, CH), 24.0 (br, 2×$CH_3$), 19.3 (br, 2×$CH_3$), 18.1 ($CH_3$, tol.).

HRMS (ESI-TOF): Simulated (MH+) 220.1808. found 220.1814.

Compound P4: 3,3-Diisopropyl-1-(4-methoxyphenyl)triaz-1-ene

The product was synthesized from lithium diisopropylamide (2.0 mmol, 214 mg), $N_2O$ and p-methoxymagnesium chloride in THF (0.92 M, 4.35 mL, 2.0 eq.) according to the general procedure. The crude product was purified by flash chromatography on deactivated silica ($NEt_3$) with a gradient of hexane to hexane/ethyl acetate (30%) as eluent. The product was obtained as a yellow oil (390 mg, yield: 83%).

$^1$H NMR (400 MHz, CDCl3, 0° C.) δ: 7.51-7.47 (m, 2H, 2×$CH_{ar}$), 6.98-6.94 (m, 2H, 2×$CH_{ar}$), 5.17-4.20 (m (br), 2H, 2×CH), 3.84 (s, 3H, OMe), 1.36 (d (br), J=6.8 Hz, 12H, 4×$CH_3$).

$^{13}$C NMR (100 MHz, $CDCl_3$, 0° C.) δ: 157.2 ($C_{ar}$), 145.7 ($C_{ar}$), 121.1 (2×$CH_{ar}$), 113.9 (2×$CH_{ar}$), 55.3 (OMe), 46.8 (2×CH), 21.7 (4×$CH_3$).

HRMS (ESI-TOF): Simulated (MH+) 236.1757. found 236.1761.

Compound P5: 3,3-Diisopropyl-1-(thiophen-2-yl)triaz-1-ene

The product was synthesized from lithium diisopropylamide (2.0 mmol, 214 mg), $N_2O$ and 2-thienylmagnesium chloride in THF (0.92 M, 4.35 mL, 2.0 eq.) according to the general procedure. The crude product was purified by distillation using a cold finger. The product was thus obtained as a yellow crystalline solid (176 mg, 42%).

$^1$H NMR (400 MHz, $CDCl_3$, 0° C.) δ: 6.90 (dd, J=5.3, 3.7 Hz, 1H, $CH_{ar}$), 6.87 (dd, J=3.7, 1.5 Hz, 1H, $CH_{ar}$), 6.84 (dd, J=5.3, 1.5 Hz, 1H, $CH_{ar}$), 5.33-4.98 (m, 1H, CH), 4.13-3.70 (m, 1H, CH), 1.50-1.23 (m, 6H, 2×$CH_3$), 1.35-1.07 (m, 6H, 2×$CH_3$).

$^{13}$C NMR (100 MHz, $CDCl_3$, 0° C.) δ 159.0 ($C_{ar}$), 126.1 ($CH_{ar}$), 118.6 ($CH_{ar}$), 116.9 ($CH_{ar}$), 48.8 (br, CH), 46.4 (br, CH), 24.1 (br, 2×$CH_3$), 19.5 (br, 2×$CH_3$).

HRMS (ESI-TOF): Simulated ($MH^+$) 212.1216. found 212.1221.

Compound P6: 1-(4-Fluorophenyl)-3,3-diisopropyltriaz-1-ene

The product was synthesized from lithium diisopropylamide (2.0 mmol, 214 mg), $N_2O$ and p-fluorophenylmagnesium chloride in THF (0.92 M, 4.35 mL, 2.0 eq.) according to the general procedure. The crude product was purified by flash chromatography on deactivated silica ($NEt_3$) with a gradient of hexane to hexane/ethyl acetate (5%) as eluent. The product was obtained as an yellow oil (372 mg, yield: 83%).

$^1$H NMR (400 MHz, $CDCl_3$, 0° C.) δ: 7.30-7.26 (m, 2H, 2×6.95-6.88 (m, 2H, 2×5.31-5.06 (m (br), 1H, CH), 4.01-3.66 (m (br), 1H, CH), 1.40-1.12 (m (br), 6H, 2×$CH_3$), 1.23-1.00 (m (br), 6H, 2×$CH_3$).

$^{13}$C NMR (100 MHz, $CDCl_3$, 0° C.) δ: 160.4 (d, J=242.4 Hz, CF), 148.1 (d, J=2.7 Hz, $C_{ar}$), 121.4 (d, J=7.9 Hz, 2×$CH_{ar}$), 115.4 (d, J=22.2 Hz, 2×$CH_{ar}$), 48.5 (br, CH), 45.6 (br, CH), 24.1 (br, 2×$CH_3$), 19.5 (br, 2×$CH_3$).

HRMS (ESI-TOF): Simulated (MH+) 224.1558. found 224.1562.

Compound P7: 1-((4-Fluorophenyl)diazenyl)pyrrolidine

The product was synthesized from lithiumpyrrolidinide (2.0 mmol, 154 mg), $N_2O$ and p-fluorophenylmagnesium chloride in THF (0.92 M, 4.35 mL, 2.0 eq.) according to the general procedure. The crude product was distilled under vacuum at 80° C. using a cold finger. The product was obtained as a pale yellow, crystalline solid (239 mg, yield: 62%).

¹H NMR (400 MHz, CDCl₃, 0° C.) δ: 7.39-7.33 (m, 2H, 2×CH$_{ar}$), 7.04-6.98 (m, 2H, 2×CH$_{ar}$), 4.01-3.71 (m (br), 2H, NCH₂), 3.83-3.55 (m (br), 2H, NCH₂), 2.10-1.93 (m (br), 4H, 2×CH₂).

¹³C NMR (100 MHz, CDCl₃, 0° C.) δ: 160.6 (d, J=243.0 Hz, CF), 147.8 (d, J 2.8 Hz, C$_{ar}$), 121.5 (d, J=8.0 Hz, CH$_{ar}$), 115.6 (d, J=22.3 Hz, CH$_{ar}$), 51.1 (br, NCH₂), 46.4, NCH₂), 23.9 (br, 2×CH₂).

HRMS (ESI-TOF): Simulated (MH+) 194.1088. found 194.1093.

Compound 1:
3,3-Diisopropyl-1-(phenylethynyl)triaz-1-ene

The product was synthesized from lithium diisopropylamide (3.0 mmol, 321 mg), N₂O and phenethynylmagnesium bromide in THF (0.71 M, 8.49 mL, 2.0 eq.) according to the general procedure. After filtration and removal of the solvent under reduced pressure, the crude product was purified by fractionated recrystallization from pentane at −20° C. The product was obtained as a white crystalline solid (447 mg, yield: 65%).

¹H NMR (400 MHz, CDCl₃) δ: 7.46-7.44 (m, 2H, 2×CH$_{ar}$), 7.31-7.20 (m, 3H, 3×CH$_{ar}$), 5.12 (sept, J=6.8 Hz, 1H, CH), 4.05 (sept, J=6.8 Hz, 1H, CH), 1.38 (d, J=6.8 Hz, 6H, 2×CH₃), 1.24 (d, J=6.8 Hz, 6H, 2×CH₃).

¹³C NMR (100 MHz, CDCl₃): 131.2 (2×CH$_{ar}$), 128.3 (2×CH$_{ar}$) 127.1 (CH$_{ar}$), 124.9 (C$_{ar}$), 94.0 (C$_{sp}$), 80.2 (C$_{sp}$), 50.5 (CH), 47.5 (CH), 23.5 (2×CH₃), 19.2 (2×CH₃).

HRMS (ESI-TOF): Simulated (MH+) 230.1657. found 230.1655.

Compound 2: 1-(3,3-Dimethylbut-1-ynyl)-3,3-diisopropyltriaz-1-ene

The product was synthesized from lithium diisopropylamide (3.0 mmol, 321 mg), N₂O and tert-butylethynylmagnesium bromide in THF (0.70 M, 8.57 mL, 2.0 eq.) according to the general procedure. The product was obtained as a white, crystalline solid (521 mg, yield: 83%).

¹H NMR (400 MHz, CDCl₃) δ: 5.08-4.97 (m (br), 1H, CH), 4.02-3.93 (m (br), 1H, CH), 1.32 (d (br), J=6.0 Hz, 6H, 2×CH₃), 1.31 (s, 9H, tBu), 1.18 (d (br), J=6.0 Hz, 6H, 2×CH₃).

¹³C NMR (100 MHz, CDCl₃) δ: 88.5 (C$_{sp}$), 84.2 (C$_{sp}$), 49.9 (br, CH), 46.7 (br, CH), 31.7 (3×CH₃, tBu), 28.2 (C$_{sp}$³), 23.5 (br, 2×CH₃), 19.3 (br, 2×CH₃).

HRMS (ESI-TOF): Simulated (MH+) 210.1970. found 210.1976.

Compound 3:
1-((3,3-Dimethylbut-1-ynyl)diazenyl)piperidine

The product was synthesized from lithium piperidinide (2.0 mmol, 182 mg), N₂O and tert-butylethynylmagnesium bromide in THF (0.70 M, 5.71 mL, 4.0 mmol, 2.0 eq.) according to the general procedure. The product was obtained as a brown solid (251 mg, yield: 65%).

¹H NMR (400 MHz, CDCl₃) δ: 3.73-3.67 (m (br), 4H, 2×NCH₂), 1.74-1.63 (m (br), 4H, 2×CH₂), 1.63-1.53 (m (br), 2H, CH₂) 1.27 (s, 9H, tBu).

¹³C NMR (100 MHz, CDCl₃) δ: 90.1 (C$_{sp}$), 83.2 (C$_{sp}$), 53.2 (NCH₂), 43.5 (NCH₂), 31.4 (3×CH₃, tBu), 28.1 (C$_{sp}$³), 26.2 (CH₂), 24.3 (CH₂), 24.0 (CH₂).

HRMS (ESI-TOF): Simulated (MH+) 194.1657. found 194.1654.

Compound 4: 1-(3,3-Dimethylbut-1-ynyl)-3-isopropyl-3-methyltriaz-1-ene

The product was synthesized from lithium isopropyl (methyl)amide (2.0 mmol, 158 mg), N₂O and tert-butylethynylmagnesium bromide in THF (0.70 M, 5.71 mL, 4.0 mmol, 2.0 eq.) according to the general procedure. The product was obtained as a pale yellow crystalline solid (265 mg, yield: 73%).

¹H NMR (400 MHz, CDCl₃) δ: 4.21 (hept, J=6.7 Hz, 1H, CH), 2.96 (s, 3H, NMe), 1.26 (s, 9H, tBu), 1.25 (d, J=6.7 Hz, 6H, 2×CH₃).

¹³C NMR (100 MHz, CDCl₃) δ: 88.0 (C$_{sp}$), 83.8 (C$_{sp}$), 57.1 (CH), 31.5 (3×CH₃, tBu), 30.8 (NMe), 28.1 (C$_{sp}$³), 20.7 (2×CH₃).

HRMS (ESI-TOF): Simulated (MH+) 182.1657. found 182.1656.

Compound 5:
1-(3,3-Dimethylbut-1-ynyl)-3,3-dimethyltriaz-1-ene

The product was synthesized from lithium dimethylamide (2.0 mmol, 102 mg), N₂O and tert-butylethynylmagnesium bromide in THF (0.70 M, 5.71 mL, 4.0 mmol, 2.0 eq.) according to the general procedure. The product was obtained as a pale yellow crystalline solid (93 mg, yield: 30%).

¹H NMR (400 MHz, CDCl₃) δ: 3.41 (s (br), 3H, NMe), 3.04 (s (br), 3H, NMe), 1.23 (s, 9H, tBu).

¹³C NMR (100 MHz, CDCl₃) δ: 88.5 (C$_{sp}$), 83.5 (C$_{sp}$), 43.3 (NMe), 36.1 (NMe), 31.4 (3×CH₃, tBu), 28.0 (C$_{sp}$³)

HRMS (APPI-Orbitrap): Simulated (MH+) 154.1339. found 154.1341.

Compound 6:
1-(Hex-1-ynyl)-3,3-diisopropyltriaz-1-ene

The product was synthesized from lithium diisopropylamide (3.0 mmol, 321 mg), N₂O and n-hexynylmagnesium bromide in THF (0.54 M, 6.0 mmol, 11.11 mL, 2.0 eq.) according to the general procedure. The product was obtained as a yellow oil (581 mg, yield: 93%).

¹H NMR (400 MHz, CDCl₃) δ: 4.92-4.77 (m (br), 1H, CH), 3.94-3.72 (m (br), 1H, CH), 2.30 (t, J=7.2 Hz, 2H, NCH₂), 1.44-1.35 (m, 2H, CH₂), 1.35-1.25 (m, 2H, CH₂), 1.16 (d (br), J=5.6 Hz, 6H, 2×CH₃), 1.03 (d, J=6.0 Hz, 6H, 2×CH₃), 0.77 (t, J=7.2 Hz, 3H, CH₃).

¹³C NMR (100 MHz, CDCl₃) δ: 85.0 (C$_{sp}$), 79.4 (C$_{sp}$), 49.4 (br, CH), 46.3 (br, CH), 31.2 (CH₂), 23.1 (2×CH₃, iPr), 21.8 (CH₂), 19.0 (CH₂) 18.7 (2×CH₃, iPr), 13.4 (CH₃, nBu).

HRMS (ESITOF): Simulated (MH+) 210.1970. found 210.1980.

Compound 7: 3,3-Diisopropyl-1-(3-methoxyprop-1-ynyl)triaz-1-ene

The product was synthesized from lithium diisopropylamide (2.0 mmol, 214 mg), N₂O and (3-methoxyprop-1-yn-1-yl)magnesium bromide in THF (0.64 M, 6.22 mL, 4.0 mmol, 2.0 eq.) according to the general procedure. The product was obtained as a brown oil (331 mg, yield: 84%).

¹H NMR (400 MHz, CDCl₃) δ: 5.04 (hept, J=6.8 Hz, 1H, CH), 4.40 (s, 2H, CH₂), 4.01 (hept, J=6.8 Hz, 1H), 3.42 (s, 3H, OMe), 1.32 (d, 6H, J=6.8 Hz, 2×CH₃), 1.20 (d, J=6.8 Hz, 6H, 2×CH₃).

$^{13}$C NMR (100 MHz, CDCl$_3$) δ: 90.7 (C$_{sp}$), 74.5 (C$_{sp}$), 61.0 (OMe), 57.5 (OCH$_2$), 50.4 (CH), 47.4 (CH), 23.5 (2×CH$_3$), 19.1 (2×CH$_3$).

HRMS (ESI-TOF): Simulated (MH+) 198.1606. found 198.1609.

Compound 8: 3-(3,3-Diisopropyltriaz-1-enyl)-N,N-dimethylprop-2-yn-1-amine

The product was synthesized from lithium diisopropylamide (2.0 mmol, 214 mg), N$_2$O and (3-(dimethylamino)prop-1-yn-1-yl)magnesium bromide in THF (0.63 M, 6.31 mL, 4.0 mmol, 2.0 eq.) according to the general procedure. The product was obtained as a brown oil (366 mg, yield: 87%).

$^1$H NMR (400 MHz, CDCl$_3$) δ: 4.98 (hept, J=6.6 Hz, 1H, CH), 3.93 (hept, J=6.6 Hz, 1H, CH), 3.49 (s, 2H, CH$_2$), 2.28 (s, 6H, NMe$_2$), 1.27 (d, J=6.6 Hz, 6H, 2×CH$_3$), 1.14 (d, J=6.6 Hz, 6H, 2×CH$_3$).

$^{13}$C NMR (100 MHz, CDCl$_3$) δ: 89.7 (C$_{sp}$), 73.7 (C$_{sp}$), 49.9 (CH), 48.9 (CH$_2$), 46.9 (CH), 44.2 (NMe), 23.4 (2×CH$_3$), 19.1 (2×CH$_3$).

HRMS (ESI-TOF): Simulated (MH+) 211.1923. found 211.1921.

Compound 9: 3-Isopropyl-1-(3-methoxyprop-1-ynyl)-3-methyltriaz-1-ene

The product was synthesized from lithium isopropyl(methyl)amide (2.0 mmol, 158 mg), (2.0 mmol, 214 mg), N$_2$O and (3-methoxyprop-1-yn-1-yl)magnesium bromide in THF (0.64 M, 6.22 mL, 4.0 mmol, 2.0 eq.) according to the general procedure. The crude product was purified by flash chromatography on deactivated silica (NEt$_3$) with a gradient of hexane/ethyl acetate (5%) to hexane/ethyl acetate (20%) as eluent. The product was obtained as a colorless oil (169 mg, yield: 50%).

$^1$H NMR (400 MHz, CDCl$_3$) δ: 4.38 (s, 2H, CH$_2$), 4.20 (hept, J=6.8 Hz, 1H, CH), 3.41 (s, 3H, OMe), 3.04 (s, 3H, NMe), 1.30 (d, J=6.8 Hz, 6H, 2×CH$_3$).

$^{13}$C NMR (100 MHz, CDCl$_3$) δ: 90.3 (C$_{sp}$), 73.9 (C$_{sp}$), 60.8 (OMe), 57.7 (CH), 57.4 (CH$_2$), 31.8 (NMe), 20.8 (2×CH$_3$).

HRMS (ESI-TOF): Simulated (MH+) 170.1288. found 170.1287.

Compound 10: 3-(3-Isopropyl-3-methyltriaz-1-enyl)-N,N-dimethylprop-2-yn-1-amine The product was synthesized from lithium isopropyl(methyl)amide (2.0 mmol, 158 mg), N$_2$O and (3-(dimethylamino)prop-1-yn-1-yl) magnesium bromide in THF (0.63 M, 6.31 mL, 4.0 mmol, 2.0 eq.) according to the general procedure. The crude product was purified by flash chromatography on deactivated silica (NEt3) with ethyl acetate as eluent. The product was obtained as a yellow oil (190 mg, yield: 52%).

$^1$H NMR (400 MHz, CDCl$_3$) δ: 4.19 (hept, J=6.8 Hz, 1H, CH), 3.53 (s, 2H, CH$_2$), 3.01 (s, 3H, NMe), 2.31 (s, 6H, NMe$_2$), 1.29 (d, J=6.8 Hz, 6H, 2×CH$_3$).

$^{13}$C NMR (100 MHz, CDCl$_3$) δ: 89.4 (C$_{sp}$), 73.3 (C$_{sp}$), 57.5 (CH), 48.8 (CH$_2$), 44.2 (NMe$_2$), 31.5 (NMe), 20.8 (2×CH$_3$).

HRMS (ESI-TOF): Simulated (MH+) 183.1604. found 183.1603.

Compound 11: 3-Cyclohexyl-1-(hex-1-ynyl)-3-methyltriaz-1-ene

The product was synthesized from lithium cyclohexylmethylamide (2.0 mmol, 214 mg), N$_2$O and n-hexynylmagnesium bromide in THF (0.54 M, 4.0 mmol 7.41 mL, 2.0 eq.)) according to the general procedure. After filtration and removal of the solvent under reduced pressure, the crude product was purified by flash chromatography with on deactivated silica (NEt$_3$) with hexane/ethyl acetate (5%) as eluent. The product was obtained as a colorless oil (249 mg, 56%).

$^1$H NMR (400 MHz, CDCl$_3$) δ 3.74 (tt, J=12.1, 3.6 Hz, 1H, CH), 3.02 (s, 3H, NMe), 2.44 (t, J=7.0 Hz, 2H, CH$_2$), 1.90-1.81 (m, 4H, 2×CH$_2$), 1.70-1.64 (m, 1H, CHH), 1.59-1.51 (m, 4H, 2×CH$_2$), 1.48-1.40 (m, 2H, CH$_2$), 1.37-1.26 (m, 2H, CH$_2$), 1.19-1.11 (m, 1H, CHH), 0.90 (t, J=7.3 Hz, 3H, CH$_3$).

$^{13}$C NMR (100 MHz, CDCl$_3$) δ: 85.1 (C$_{sp}$), 79.5 (C$_{sp}$), 65.3 (CH), 32.3 (NCH$_3$), 31.5 (CH$_2$), 31.3 (2×CH$_2$), 25.6 (2×CH$_2$), 25.4 (CH$_2$), 22.2 (CH$_2$), 19.2 (CH$_2$), 13.8 (CH$_3$).

HRMS (ESI-TOF): Simulated (MH$^+$) 222.1970. found 222.1973.

Compound 12: 1-(3,3-Dimethylbut-1-ynyl)-3,3-diethyltriaz-1-ene

The product was synthesized from lithium diethylamide (2.0 mmol, 163 mg), N$_2$O and tert-butylethynylmagnesium bromide in THF (0.70 M, 5.71 mL, 4.0 mmol, 2.0 eq.) according to the general procedure. The product was obtained as an orange oil (163 mg, yield: 45%).

$^1$H NMR (400 MHz, CDCl$_3$, 0° C.) δ: 3.68 (q, J=7.2 Hz, 1H), 3.58 (q, J=7.1 Hz, 1H), 1.23 (s, 4H), 1.21 (t, J=7.3 Hz, 2H), 1.08 (t, J=7.1 Hz, 2H).

$^{13}$C NMR (100 MHz, CDCl$_3$, 0° C.) δ: 88.3 (C$_{sp}$), 83.8 (C$_{sp}$), 49.5 (br, CH$_2$), 41.5 (br, CH$_2$), 31.6 (3×CH$_3$, tBu), 28.1 (C$_{sp}^3$), 14.4 (br, CH$_3$), 11.1 (br, CH$_3$).

HRMS (ESI-TOF): Simulated (MH+) 182.1657. found 182.1655.

Compound 13: 3,3-Dimethyl-1-(phenylethynyl)triaz-1ene

The product was synthesized from lithium dimethylamide (2.0 mmol, 214 mg), N$_2$O and phenethynylmagnesium bromide in THF (0.71 M, 8.49 mL, 4.0 mmol, 2.0 eq.) according to the general procedure. The product was obtained as a brown solid (163 mg, yield: 47%).

$^1$H NMR (400 MHz, CDCl$_3$) δ: 7.39-7.34 (m, 2H, 2×CH$_{ar}$), 7.28-7.15 (m, 3H, 3×CH$_{ar}$), 3.47 (s, 3H, CH$_3$), 3.13 (s, 3H, CH$_3$).

$^{13}$C NMR (100 MHz, CDCl$_3$) δ: 131.2 (2×CH$_{ar}$), 128.2 (2×CH$_{ar}$), 127.2 (CH$_{ar}$), 124.3 (C$_{ar}$), 93.0 (C$_{sp}$), 80.1 (C$_{sp}$), 43.7 (CH$_3$), 36.6 (CH$_3$).

HRMS (APPI-Orbitrap): Simulated (MH+) 173.0948. found 173.0945.

Compound 14: 1-(3-Methoxyprop-1-ynyl)-3,3-dimethyltriaz-1-ene

The product was synthesized from lithium diisopropylamide (2.0 mmol, 214 mg), N$_2$O and (3-methoxyprop-1-yn-1-yl)magnesium bromide in THF (0.64 M, 6.22 mL, 4.0 mmol, 2.0 eq.) according to the general procedure. The product was obtained as an yellow oil (51 mg, yield: 18%).

¹H NMR (400 MHz, CDCl₃) δ: 4.34 (s, 2H, CH₂), 3.47 (3.41 (s, 3H, NMe), 3.37 (s, 3H, OMe), 3.11 (s, 3H, NMe).
¹³C NMR (100 MHz, CDCl₃) δ: 89.8 ($C_{sp}$), 74.3 ($C_{sp}$), 60.6 (OMe), 57.3 (CH₂), 43.6 (NMe), 36.4 (NMe).
HRMS (ESI-TOF): Simulated (MH+) 142.0980. found 142.0986.

Compound 15: 3-(3,3-Dimethyltriaz-1-enyl)-N,N-dimethylprop-2-yn-1-amine

The product was synthesized from lithium diisopropylamide (2.0 mmol, 214 mg), N₂O and (3-(dimethylamino)prop-1-yn-1-yl)magnesium bromide in THF (0.63 M, 6.31 mL, 4.0 mmol, 2.0 eq.) according to the general procedure. The product was obtained as a yellow oil (99 mg, yield: 32%).
¹H NMR (400 MHz, CDCl₃) δ: 3.55 (s, 2H, CH₂), 3.48 (s, 3H, (N=NNMe)CH₃), 3.13 (s, 3H, (N=N—NMe)CH₃), 2.32 (s, 6H (CH₂N)Me₂).
¹³C NMR (100 MHz, CDCl₃) δ: 89.0 ($C_{sp}$), 73.6 ($C_{sp}$), 48.6 (CH₂), 44.0 ((CH₂N)Me₂), 43.4 ((N=N—NMe)CH₃), 36.2 ((N=N—NMe)CH₃).
HRMS (ESI-TOF): Simulated (MH+) 155.1297. found 155.1294.

Compound 16: 3,3-Diisopropyl-1-(2-methylprop-1-enyl)triaz-1-ene

The product was synthesized from lithium diisopropylamide (3.0 mmol, 321 mg), N₂O and 2-methyl-1-propenylmagnesium bromide in THF (0.54 M, 6.0 mmol, 11.11 mL, 2.0 eq.) according to the general procedure. The crude product was purified by flash chromatography on deactivated silica (NEt₃) with a gradient of hexane to hexane/ethyl acetate (5%) as eluent. The product was obtained as a colorless oil (484 mg, yield: 88%).
¹H NMR (400 MHz, CDCl₃) δ: 6.78 (qq, J=1.2 Hz, J=1.2 Hz, 1H, $CH_{olef}$), 4.73-4.15 (m (br), 2H, 2×CH), 1.99 (m, 3H, CH₃, dimethylvinyl), 1.81-1.80 (m, 3H, CH₃, dimethylvinyl), 1.25 (d, J=6.8 Hz, 6H, 2×CH₃, iPr).
¹³C NMR (100 MHz, CDCl₃) δ: 138.0 ($CH_{olef}$), 125.9 ($C_{olef}$), 47.1 (br, 2×CH), 22.8 (CH₃, dimethylvinyl), 21.5 (br, 4×CH₃, iPr), 17.5 (CH₃, dimethylvinyl).
HRMS (ESI-TOF): Simulated (MH+) 184.1814. found 184.1808.

Compound 17:
1-Cyclohexenyl-3,3-diisopropyltriaz-1-ene

The product was synthesized from lithium diisopropylamide (2.0 mmol, 214 mg), N₂O and 1-cyclohexenylmagnesium bromide in THF (0.33 M, 4.0 mmol, 12.12 mL, 2.0 eq.) according to the general procedure. The crude product was purified by flash chromatography on deactivated silica (NEt₃) with a gradient of hexane to hexane/ethyl acetate (5%) as eluent. The product was obtained as a colorless oil (310 mg, yield: 74%).
¹H NMR (400 MHz, CDCl₃) δ: 5.84 (tt, J=4.2, 1.4 Hz, 1H, $CH_{olef}$), 4.70-4.32 (m, 2H, 2×CH), 2.36-2.32 (m, 2H, CH₂), 2.25-2.21 (m, 2H, CH₂), 1.75-1.69 (m, 2H, CH₂), 1.65-1.60 (m, 2H, CH₂), 1.21 (d, J=6.7 Hz, 12H, 4×CH₃).
¹³C NMR (100 MHz, CDCl₃) δ: 149.8 ($C_{olef}$), 120.0 ($CH_{olef}$), 46.2 (br, CH), 25.3 (CH₂), 24.3 (CH₂), 23.1 (CH₂), 23.0 (CH₂), 21.7 (br, 4×CH₃).
HRMS (ESI-TOF): Simulated (MH+) 210.1970. found 210.1971.

Compound 18:
1-Cyclohexenyl-3-isopropyl-3-methyltriaz-1-ene

The product was synthesized from lithium isopropyl (methyl)amide (2.0 mmol, 158 mg), N₂O and 1-cyclohexenylmagnesium bromide in THF (0.33 M, 4.0 mmol, 12.12 mL, 2.0 eq.) according to the general procedure. The crude product was purified by flash chromatography on deactivated silica (NEt₃) with a gradient of hexane to hexane/ethyl acetate (5%) as eluent. The product was obtained as a colorless oil (265 mg, yield: 73%).
¹H NMR (400 MHz, CDCl₃) δ: 5.91 (tt, J=4.2, 1.3 Hz, 1H, $CH_{olef}$), 4.06 (hept, J=6.6 Hz, 1H, CH), 2.95 (s, 3H, NMe), 2.33-2.29 (m, 2H, CH₂), 2.24-2.20 (m, 2H, CH₂), 1.74-1.68 (m, 2H, CH₂), 1.64-1.59 (m, 2H, CH₂), 1.24 (d, J=6.7 Hz, 6H).
¹³C NMR (100 MHz, CDCl₃) δ: 149.4 ($C_{olef}$), 121.2 ($CH_{olef}$), 55.5 (CH), 31.1 (NMe), 25.3 (CH₂), 24.3 (CH₂), 23.0 (CH₂), 22.9 (CH₂), 20.8 (2×CH₃).
HRMS (ESI-TOF): Simulated (MH+) 182.1657. found 182.1654.

Compound 19: 3-Isopropyl-3-methyl-1-(2-methylprop-1-enyl)triaz-1-ene

The product was synthesized from lithium isopropyl (methyl)amide (2.0 mmol, 158 mg), N₂O and 2-methyl-1-propenylmagnesium bromide in THF (0.54 M, 4.0 mmol, 7.41 mL, 2.0 eq.) according to the general procedure. The crude product was purified by flash chromatography on deactivated silica (NEt₃) with a gradient of pentane to pentane/diethyl ether (5%) as eluent. The product was thus obtained as a colorless (volatile) oil (58 mg, yield: 19%).
¹H NMR (400 MHz, CDCl₃) δ: 6.77-6.76 (m, 1H, $CH_{olef}$), 4.11 (hept, J=6.5 Hz, 1H, CH), 2.94 (s, 2H, NMe), 1.98 (s, 3H, CH₃, dimethylvinyl), 1.79 (s, 3H, CH₃, dimethylvinyl), 1.24 (d, J=6.8 Hz, 4H, 2×CH₃, iPr).
¹³C NMR (100 MHz, CDCl₃) δ: 137.4 ($CH_{olef}$), 127.8 ($C_{olef}$), 55.1 (br, CH), 30.9 (NMe), 22.9 (CH₃, dimethylvinyl), 22.7 (br, 2×CH₃, iPr), 17.6 (CH₃, dimethylvinyl).
HRMS (ESI-TOF): Simulated (MH+) 156.1501. found 156.1503.

Compound 20: 3,3-Dicyclohexyl-1-vinyltriaz-1-ene

The product was synthesized from lithium dicyclohexylamide (2.0 mmol, 374 mg), N₂O and vinylmagnesium bromide in THF (1.80 M, 8.49 mL, 2.0 eq.) according to the general procedure. After filtration and removal of the solvent under reduced pressure, the crude product was purified by flash chromatography with on deactivated silica (NEt₃) with a gradient of hexane to hexane/ethyl acetate (5%) as eluent. The product was obtained as a white solid (423 mg, 90%).
¹H NMR (400 MHz, CDCl₃, 0° C.) δ 7.16 (dd, J=15.5, 7.8 Hz, 1H, $CH_{olef}$), 5.17 (d, J=15.5 Hz, 1H, $CH_{olef}$), 5.00-4.82 (m, 1H, CH), 4.76 (d, J=8.1 Hz, 1H, $CH_{olef}$), 3.53-3.22 (m, 1H, CH), 1.84-1.64 (m, 12H, 6×CH₂), 1.49-1.25 (s, 6H, 3×CH₂), 1.19-1.07 (d, 2H, 1×CH₂).
¹³C NMR (100 MHz, CDCl₃) δ 149.2 ($CH_{olef}$), 104.5 ($CH_{2,olef}$), 56.9 (br, CH), 53.5 (br, CH), 34.1 (br, 2×CH₂), 29.9 (br, 2×CH₂), 26.2 (br, 2×CH₂), 25.7 (br, 3×CH₂), 25.4 (CH₂).
HRMS (ESI-TOF): Simulated (MH⁺) 236.2127. found 237.2157.

Compound 21:
1-(1,2-Diphenylvinyl)-3,3-diisopropyltriaz-1-ene

The product was synthesized from lithium diisopropylamide (2.0 mmol, 214 mg), N₂O, and (E)-(1,2-diphenylvinyl)magnesium bromide in THF (0.66 M, 6.00 mL, 4.0 mmol) according to the general procedure. The crude product was purified by flash chromatography with a gradient of hexane to hexane/ethyl acetate (10%). The product was obtained as a mixture of the E and Z isomer as a yellow oil (440 mg, 72%).

An attribution of the spectra to the respective isomers was attempted by 1D-NOESY and HMBC experiments, indicating that Isomer 1 (39%) is the E isomer and Isomer 2 (61%) is the Z isomer.

Isomer 1:
$^1$H NMR (400 MHz, CDCl$_3$, 0° C.) δ: 7.81 (d, J=7.3 Hz, 2H, CH$_{ar}$), 7.37-6.97 (m, 9H, 9×CH$_{ar}$), 6.17 (s, 1H, CH$_{olef}$), 5.39 (hept, J=6.8 Hz, 1H, CH), 3.86 (hept, J=6.6 Hz, 1H, CH), 1.25 (d, J=6.8 Hz, 6H), 1.10 (d, J=6.6 Hz, 6H).
$^{13}$C NMR (100 MHz, CDCl$_3$) δ: 151.1 (C$_{olef/ar}$), 140.6 (C$_{olef/ar}$), 137.6 (C$_{olef/ar}$), 130.0 (2×CH$_{ar}$), 129.2 (2×CH$_{ar}$), 128.0 (2×CH$_{ar}$), 127.3 (2×CH$_{ar}$), 126.9 (CH$_{ar}$), 125.9 (CH$_{ar}$), 119.4 (CH$_{olef}$), 48.5 (CH), 45.8 (CH), 23.8 (2×CH$_3$), 19.5 (2×CH$_3$).

Isomer 2:
$^1$H NMR (400 MHz, CDCl$_3$) δ: 7.37-6.97 (m, 10H, 10×CH$_{ar}$), 6.77 (s, 1H, CH$_{olef}$), 5.39-5.16 (m (br), 1H, CH), 3.88-3.66 (m (br), 1H, CH), 1.23-1.09 (m (br), 6H, 2×CH$_3$), 1.09-0.93 (m (br), 6H, 2×CH$_3$).
$^{13}$C NMR (100 MHz, CDCl$_3$) δ: 152.7 (C$_{olef/ar}$), 137.9 (C$_{olef/ar}$), 137.2 (C$_{olef/ar}$), 130.0 (2×CH$_{ar}$), 129.0 (2×CH$_{ar}$), 128.0 (2×CH$_{ar}$), 127.9 (2×CH$_{ar}$), 127.1 (CH$_{ar}$), 125.8 (CH$_{ar}$), 121.8 (CH$_{olef}$), 48.2 (CH), 45.1 (CH), 23.6 (2×CH$_3$), 19.5 (2×CH$_3$).

HRMS (mixture of isomers, ESI-TOF) Simulated (MH$^+$) 308.2127. found 308.2119.

Compound 22: 3,3-Diisopropyl-1-styryltriaz-1-ene

The product was synthesized from lithium diisopropylamide (2.0 mmol, 214 mg), N$_2$O and β-stryrylmagnesium bromide (E/Z of the bromide=89:11) in THF (0.71 M, 8.49 mL, 2.0 eq.) according to the general procedure. After filtration and removal of the solvent under reduced pressure, the crude product was purified by flash chromatography with on deactivated silica (NEt$_3$) with a gradient of hexane to hexane/ethyl acetate (5%) as eluent. The minor E isomer was obtained as a pale yellow solid (13 mg). The Z isomer was obtained as a pale yellow oil (203 mg). The total isolated yield of both isomers (E/Z=94:6) was 216 mg (47%).

E-isomer:
$^1$H NMR (400 MHz, CDCl$_3$, 0° C.) δ 7.61 (d, J=14.1 Hz, 1H, CH$_{olef}$), 7.28-7.26 (m, 2H, 2×CH$_{ar}$), 7.15-7.11 (m, 2H, 2×CH$_{ar}$), 7.02-6.98 (m, 1H, CH$_{ar}$), 6.50 (d, J=14.1 Hz, 1H, CH$_{olef}$), 5.15-5.00 (m (br), 1H, CH), 3.84-3.65 (m (br), 1H, CH), 1.26-1.04 (m (br), 6H, 2×CH$_3$), 1.15-0.88 (m (br), 6H, 2×CH$_3$).
$^{13}$C NMR (100 MHz, CDCl$_3$) δ 143.2 (CH$_{olef}$), 137.5 (C$_{ar}$), 128.6 (2×CH$_{ar}$), 126.4 (CH$_{ar}$), 126.0 (2×CH$_{ar}$), 121.8 (CH$_{olef}$), 48.3 (CH), 45.8 (CH), 23.7 (2×CH$_3$), 19.6 (2×CH$_3$).

Z-isomer:
$^1$H NMR (400 MHz, CDCl$_3$) δ 7.79-7.77 (m, 2H, 2×CH$_{ar}$), 7.26-7.23 (m, 2H, 2×CH$_{ar}$), 7.12-7.07 (m, 1H, CH$_{ar}$), 7.06 (d, J=9.0 Hz, 1H, CH$_{olef}$), 5.79 (d, J=9.0 Hz, 1H, CH$_{olef}$), 5.13 (sept, J=6.8 Hz, 1H, CH), 3.91 (sept, J=6.8 Hz, 1H, CH), 1.26 (d, J=6.8 Hz, 6H, 2×CH$_3$), 1.19 (d, J=6.8 Hz, 6H, 2×CH$_3$).
$^{13}$C NMR (100 MHz, CDCl$_3$) δ 142.0 (CH$_{olef}$), 137.5 (C$_{ar}$), 129.6 (2×CH$_{ar}$), 128.2 (2×CH$_{ar}$), 126.0 (2×CH$_{ar}$), 117.0 (CH$_{olef}$), 48.8 (CH), 47.0 (CH), 23.7 (2×CH$_3$), 19.3 (2×CH$_3$).

HRMS (mixture of isomers, ESI-TOF): Simulated (MH$^+$) 232.1814. found 232.1805.

Compound 23: 3,3-Diisopropyl-1-((Z)-4-methoxystyryl)triaz-1-ene

The product was synthesized from lithium diisopropylamide (2.0 mmol, 214 mg), N$_2$O and (Z)-(4-methoxystyryl) magnesium bromide in THF (0.60 M, 6.66 mL, 4.0 mmol) according to the general procedure. The crude product was dissolved in a minimal amount of dichloromethane, hexane was slowly added until the solution became slightly turbid and the mixture was placed in a fridge overnight (4° C.).

The product crystallized and the supernatant solution was discarded. The crystals were powdered, washed with cold pentane (−20° C.) and dried under vacuo (298 mg, 57%).
$^1$H NMR (400 MHz, CDCl$_3$, 0° C.) δ 7.82 (d, J=8.8 Hz, 2H, 2×CH$_{ar}$), 7.06 (d, J=9.0 Hz, 1H, CH$_{olef}$), 6.88 (d, J=8.8 Hz, 2H, 2×CH$_{ar}$), 5.83 (d, J=9.0 Hz, 1H, CH$_{olef}$), 5.19 (hept, J=6.7 Hz, 1H, CH), 3.96 (hept, J=6.5 Hz, 1H, CH), 3.82 (s, 3H, OMe), 1.34 (d, J=6.6 Hz, 5H, 2×CH$_3$), 1.28 (s, 3H, 2×CH$_3$).
$^{13}$C NMR (100 MHz, CDCl$_3$, 0° C.) 5 $^{13}$C NMR (100 MHz, CDCl$_3$) δ 157.8 (C$_{ar}$), 140.1 (CH$_{olef}$), 130.9 (2×CH$_{ar}$), 130.4 (C$_{ar}$), 116.7 (CH$_{olef}$), 113.5 (2×CH$_{ar}$), 55.3 (OMe), 48.6 (CH), 46.8 (CH), 23.7 (2×CH$_3$), 19.3 (2×CH$_3$).

HRMS (ESI-TOF): Simulated (MH$^+$) 262.1919. Found 262.1914.

Synthesis of the N$_2$O Adducts

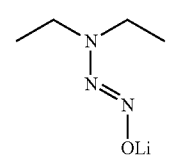

Compound I1

Lithium diethylamide (10.0 mmol, 791 mg) was dissolved in THF (10 mL). The solution was stirred for 4 h under a N$_2$O atmosphere and a white precipitate appeared. The precipitate was isolated by filtration, washed with THF (20 mL) and pentane (3×40 mL), and dried under vacuum. Yield: 1083 mg, 88%.
$^1$H NMR ([D$_6$]DMSO) δ: 2.55 (q, J=7.2 Hz, 4H, CH$_2$), 0.87 (t, J=7.2 Hz, 6H, CH$_3$).
$^{13}$C NMR ([D$_6$]DMSO) δ: 48.2 (CH$_2$), 11.9 (CH$_3$).
Elemental Analysis (C$_4$H$_{10}$LiN$_3$O): Required C, 39.03 H, 8.19 N, 34.14. Found C, 38.92 H, 8.10, N, 34.12.

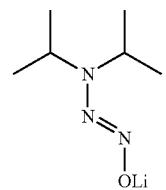

Compound I2

Lithium diisopropylamide (0.47 mmol, 50 mg) was dissolved in THF (1 mL). The solution was stirred for 4 h under an N$_2$O atmosphere and a white precipitate appeared. The precipitate was isolated by centrifugation, washed with THF (3 mL) and pentane (3×10 mL), and dried under vacuum. Yield: 67 mg, 95%.

$^1$H NMR ([D$_6$]DMSO) δ: 2.33 (sept, 6.4 Hz, 2H, CH), 0.47 (d, J=6.4 Hz, 12H, CH$_3$).

$^{13}$C NMR ([D$_6$]DMSO) δ: 49.2 (CH), 18.8 (CH$_3$).

Elemental Analysis (C$_6$H$_{15}$LiN$_3$O): Required C, 47.68 H, 9.34 N, 27.80. Found C, 47.50 H, 9.48, N, 27.68.

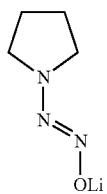

Compound I3

Lithium pyrrolidinide (10.0 mmol, 771 mg) was dissolved in THF (5 mL). The solution was stirred for 4 h under an N$_2$O atmosphere and a white precipitate appeared. The precipitate was isolated by filtration, washed with THF (20 mL) and pentane (3×40 mL), and dried under vacuum. The dried product still contained traces of THF (~8 mol %). Yield: 866 mg, 68%.

$^1$H NMR ([D$_6$]DMSO) δ: 2.76-2.73 (m, 4H, NCH$_2$), 1.65-1.62 (m, 4H, CH$_2$).

$^{13}$C NMR ([D$_6$]DMSO) δ: 52.0 (NCH$_2$), 22.6 (CH$_2$).

Elemental Analysis (C$_4$H$_8$LiN$_3$O×0.08 THF): Required C, 40.91, H, 6.87, N, 33.13. Found C, 40.74 H, 7.01, N, 33.13

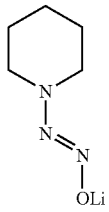

Compound I4

Lithium piperidinide (10.0 mmol, 911 mg) was dissolved in THF (10 mL). The solution was stirred for 4 h under an N$_2$O atmosphere and a white precipitate appeared. The precipitate was isolated by filtration, washed with THF (20 mL) and pentane (3×40 mL), and dried under vacuum. The dried product still contained traces of THF (~4 mol %). Yield: 1000 mg, 72%.

$^1$H NMR ([D$_6$]DMSO) δ: 2.64-2.40 (m (br), 4H, NCH$_2$), 1.55-1.53 (m, 4H, CH$_2$), 1.35-1.34 (m, 2H, CH$_2$).

$^{13}$C NMR ([D$_6$]DMSO) δ: 52.4 (NCH$_2$), 24.4 (NCH$_2$CH$_2$), 23.8 (NCH$_2$CH$_2$CH$_2$).

Elemental Analysis (C$_5$H$_{10}$LiN$_3$O×0.04 THF): Required C, 44.92, H, 7.54, N, 30.45. Found C, 44.44, H, 7.31, N, 30.21.

Cytotoxicity Tests:

MDA-MB-231 breast adenocarcinoma cells (ATCC® HTB-26™), MCF-10a human mammary epithelial cells (ATCC® CRL-10317™) and HEK293 human embryonic kidney cells (ATCC® CRL-1573™) were obtained from ATCC (Middlesex, UK), the A2780 human ovarian carcinoma cell line was obtained from the European Collection of Cell Cultures (catalogue number 93112519, Salisbury, U.K.). All cell culture media were purchased from Life Technologies (Zug, Switzerland). A2780 cells were cultured in RPMI-1640 medium (Gibco, GlutaMax), while MDA-MB-231 and HEK293 cells were cultured in Dulbecco's Modified Eagle Medium (DMEM, Gibco, GlutaMax) supplemented with 10% fetal bovine serum (FBS, Sigma-Aldrich, Buchs, Switzerland) and 1% penicillin/streptomycin (Life Technologies, Zug, Switzerland). MCF-10A were cultured in DMEM/F12 medium containing 10% horse serum and 1% antibiotics, supplemented with 10 μg/mL insulin, 20 μg/mL hydrocortisone, 20 ng/mL epidermal growth factor and 100 ng/mL cholera toxin (all from Sigma Aldrich, Buchs, Switzerland). Cells were incubated in a CO$_2$ incubator with 5% CO$_2$ and 100% relative humidity at 37° C. MTT (MTT=3-(4,5-dimethyl-2-thiazolyl)-2,5-diphenyl-2H-tetrazolium bromide) was purchased from Calbiochem (Zug, Switzerland). Cell viability was determined by the MTT assay. The absorption was read using a SpectraMax M52 microplate reader (Molecular Devices, Sunnyvale, Calif., USA).

Cells were seeded in 96-well plates as monolayers with 100 μL of cell suspension (approximately 5000 cells) per well and preincubated for 24 h in medium supplemented with 10% FBS. With the exception of dacarbazine, all compounds were dissolved in DMSO. In the case of dacarbazine, an aqueous stock solution of the monocitrate was prepared in situ and immediately used (light sensitivity). The stock solutions were serially diluted in the culture medium to the appropriate concentration, to give a final DMSO concentration of no higher than 0.5%. 100 μL of the compound solution was added to each well, and the plates were incubated for 72 h. Subsequently, MTT (5 mg/mL solution) was added to the cells and the plates were incubated for a further 2 h. The culture medium was aspirated and the purple formazan crystals formed by the mitochondrial dehydrogenase activity of vital cells were dissolved in DMSO. The optical density, directly proportional to the number of surviving cells, was quantified at 590 nm using a multiwell plate reader, and the fraction of surviving cells was calculated from the absorbance of untreated control cells. Evaluation is based on means from at least two independent experiments, each comprising triplicates per concentration level.

TABLE 1

IC50 values (μM) of selected triazenes after 72 h exposure on human ovarian cancer cells (A2780), human invasive breast cancer cells (MDA-MB-231), non-cancer human embryonic kidney cells (HEK293) and human mammary epithelial cells (MCF-10A).

| compound | A2780 | MDA-MB-231 | HEK293 | MCF-10A | SC[a] |
|---|---|---|---|---|---|
| 1 | 56 ± 4 | >500 | 44 ± 11 | 116 ± 2 | — |
| 2 | 160 ± 40 | 176 ± 60 | 125 ± 5 | 299 ± 43 | 1.7 |
| 4 | 32 ± 4 | 70 ± 10 | 29 ± 4 | 192 ± 12 | 2.7 |
| 5 | 22 ± 3 | 38 ± 3 | 19 ± 2 | 52 ± 11 | 1.4 |
| 6 | 143 ± 29 | 199 ± 21 | 165 ± 65 | 254 ± 52 | 1.2 |
| 9 | 20 ± 3 | 32 ± 4 | 14 ± 1 | 208 ± 49 | 6.5 |
| 10 | 34 ± 4 | 14 ± 2 | 21 ± 5 | 86 ± 4 | 6.1 |
| 14 | 43 ± 6 | 72 ± 9 | 24 ± 4 | 177 ± 23 | 2.5 |
| 15 | 47 ± 3 | 45 ± 15 | 15 ± 4 | 113 ± 7 | 2.4 |

[a]Sc = selectivity coefficient, IC$_{50}$ MCF-10A/IC$_{50}$ MDA-MB-231

The invention claimed is:

1. A method for preparing a triazene according to Formula (I)

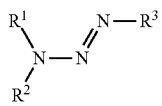
Formula (I)

comprising reacting a compound according to Formula (II)

$R^1R^2N(N_2O)M^1$   Formula (II)

with a compound according to Formula (III)

$R^3M^2$   Formula (III)

wherein
$R^1$ and $R^2$ independently are an organic residue
$R^3$ is an organic residue,
$M^1$ is a metal or metal compound, and
$M^2$ is a metal or metal compound.

2. The method according to claim 1, wherein $R^1$ and $R^2$ are independently a substituted or unsubstituted aryl group, a substituted or unsubstituted hetero aryl group, a substituted or unsubstituted alkyl group with 1 to 16 carbon atoms, a substituted or unsubstituted cyclic alkyl group with 3 to 12 carbon atoms, a substituted or unsubstituted cyclic alkenyl group with 3 to 12 carbon atoms, a substituted or unsubstituted alkenyl group with 2 to 16 carbon atoms, or a substituted or unsubstituted alkynyl group with 2 to 16 carbon atoms,
wherein in the substituted or unsubstituted alkyl group with 1 to 16 carbon atoms, the substituted or unsubstituted cyclic alkyl group with 3 to 12 carbon atoms, the substituted or unsubstituted cyclic alkyl group with 3 to 12 carbon atoms, the substituted or unsubstituted alkenyl group with 2 to 12 carbon atoms, or the substituted or unsubstituted alkynyl group with 2 to 16 carbon atoms one or more —$CH_2$— group(s) are optionally substituted by —O—, —S—, —$NR^4$—, or $SiR^4R^{4'}$ to form an ether, a thioether, a secondary or tertiary amine, or a silylether, and
wherein $R^4$ and $R^{4'}$ are independently hydrogen, an alkyl group with 1 to 6 carbon atoms or a cyclic alkyl group with 3 to 6 carbon atoms or wherein $R^1$ and $R^2$ together with the nitrogen to which $R^1$ and $R^2$ are attached form a hetero cycle with 3 to 7 carbon atoms.

3. The method according to claim 1, wherein $R^3$ is a substituted or unsubstituted aryl group, a substituted or unsubstituted hetero aryl group, a substituted or unsubstituted alkyl group with 1 to 16 carbon atoms, a substituted or unsubstituted cyclic alkyl group with 3 to 12 carbon atoms, a substituted or unsubstituted cyclic alkenyl group with 3 to 12 carbon atoms, a substituted or unsubstituted alkenyl group with 2 to 16 carbon atoms, or a substituted or unsubstituted alkynyl group with 2 to 16 carbon atoms,
wherein in the substituted or unsubstituted alkyl group with 1 to 16 carbon atoms, the substituted or unsubstituted cyclic alkyl group with 3 to 12 carbon atoms, the substituted or unsubstituted cyclic alkyl group with 3 to 12 carbon atoms, the substituted or unsubstituted alkenyl group with 2 to 12 carbon atoms, or the substituted or unsubstituted alkynyl group with 2 to 16 carbon atoms one or more —$CH_2$— group(s) are optionally substituted by —O—, —S—, —$NR^4$—, or $SiR^4R^{4'}$ to form an ether, a thioether, a secondary or tertiary amine, or silylether, and
wherein $R^4$ and $R^{4'}$ are independently hydrogen, an alkyl group with 1 to 6 carbon atoms or a cyclic alkyl group with 3 to 6 carbon atoms.

4. The method according to claim 1, wherein the compound according to Formula (II)

$R^1R^2N(N_2O)M^1$   Formula (II)

is prepared by reacting a compound according to Formula (IV)

Formula (IV)

with nitrous oxide.

5. The method according to claim 4, comprising reacting a compound according to Formula (IV) with a nitrous oxide and a compound according to Formula (III).

6. A method for preparing a compound comprising a triazene group, wherein the method comprises a reaction utilizing $N_2O$.

7. The method according to claim 6 wherein a compound according to Formula(e) (I) and/or (II) is prepared.

8. A compound according to Formula (II)

$R^1R^2N(N_2O)M^1$   Formula (II)

wherein $R^1$ and $R^2$ independently are an organic residue, and
$M^1$ is a metal compound.

9. A compound according to claim 8, wherein the compound is present in isolated form.

10. A method for preparing a compound according to Formula (II)

$R^1R^2N(N_2O)M^1$   Formula (II)

by reacting $R^1R^2N$-$M^1$ with nitrous oxide, wherein
$R^1$ and $R^2$ independently are an organic residue, and
$M^1$ is a metal or metal compound.

11. The method according to claim 1, wherein $M^1$ is a metal selected from the group consisting of Li, Na, and K.

12. The method according to claim 1, wherein $M^2$ is a metal or metal compound selected from the group consisting of Li, Na, K, MgCl, MgBr, MgI, ZnCl, ZnBr, ZnI, $ZnR^{3'}$, and Al $R^{3'}R^{3''}$, wherein $R^{3'}$ and $R^{3''}$ are independently an organic residue.

13. The compound according to claim 8, wherein $M^1$ is a metal selected from the group consisting of Li, Na, and K.

14. The compound according to claim 9, wherein the compound is present in isolated crystalline form.

15. The method according to claim 10, wherein $M^1$ is a metal selected from the group consisting of Li, Na, and K.

16. The method according to claim 1, wherein $R^1$ and $R^2$ are independently a methyl group, ethyl group, isopropyl group, or cyclohexyl group.

* * * * *